(12) United States Patent
Jia

(10) Patent No.: US 10,884,005 B2
(45) Date of Patent: Jan. 5, 2021

(54) DIABETES-RELATED BIOMARKERS AND TREATMENT OF DIABETES-RELATED CONDITIONS

(71) Applicant: Wei Jia, Honolulu, HI (US)

(72) Inventor: Wei Jia, Honolulu, HI (US)

( * ) Notice: Subject to any disclaimer, the term of this patent is extended or adjusted under 35 U.S.C. 154(b) by 191 days.

(21) Appl. No.: 15/769,037

(22) PCT Filed: Oct. 18, 2016

(86) PCT No.: PCT/US2016/057538
§ 371 (c)(1),
(2) Date: Apr. 17, 2018

(87) PCT Pub. No.: WO2017/070114
PCT Pub. Date: Apr. 27, 2017

(65) Prior Publication Data
US 2019/0285656 A1    Sep. 19, 2019

Related U.S. Application Data

(60) Provisional application No. 62/243,131, filed on Oct. 18, 2015.

(51) Int. Cl.
| | |
|---|---|
| *G01N 33/68* | (2006.01) |
| *G01N 33/92* | (2006.01) |
| *G16C 20/30* | (2019.01) |
| *C07J 9/00* | (2006.01) |
| *C07J 41/00* | (2006.01) |
| *G16B 25/00* | (2019.01) |

(52) U.S. Cl.
CPC .............. *G01N 33/92* (2013.01); *C07J 9/005* (2013.01); *C07J 41/0061* (2013.01); *G01N 33/6893* (2013.01); *G16B 25/00* (2019.02); *G16C 20/30* (2019.02); *G01N 2800/042* (2013.01); *G01N 2800/50* (2013.01); *G01N 2800/52* (2013.01); *G01N 2800/60* (2013.01)

(58) Field of Classification Search
CPC . C07J 41/0061; C07J 9/005; G01N 2800/042; G01N 2800/50; G01N 2800/52; G01N 33/6893; G01N 33/92; G16C 20/30
See application file for complete search history.

(56) References Cited

U.S. PATENT DOCUMENTS

| | | | | |
|---|---|---|---|---|
| 2009/0239253 | A1* | 9/2009 | Watkins | ............. G01N 33/6893 435/29 |
| 2011/0311650 | A1* | 12/2011 | Wang | ................. G01N 33/6893 424/646 |

* cited by examiner

*Primary Examiner* — Jennifer Wecker
(74) *Attorney, Agent, or Firm* — Hawaii Patent Services; Nathaniel K. Fedde

(57) ABSTRACT

The present invention provides biomarkers useful for evaluating the risk that a subject will develop diabetes, monitoring such risk, identifying members of a population at risk of developing diabetes, calculating risk of a subject developing diabetes, advising subjects of risk for developing diabetes, providing diagnostic tests for identifying subjects at risk for developing diabetes or kits there for, and providing diagnostic tests for determining risk of a subject developing diabetes and kits there for. The present invention also provides compounds and methods for treating subjects.

19 Claims, 16 Drawing Sheets

| Bile Acids | Amino Acids | Free Fatty Acids | Amino Acids | Blood biochemical Index biomarkers |
|---|---|---|---|---|
| GHDCA | Aspartic acid | C16:0/C18:0 | Isoleucine | TG |
| TCDCA | Beta-Alanine | C18:1 n9/C18:0 | Leucine | HBA1c |
| TDCA | Creatine | C20:3 n6/C20:4 | Tyrosine | Glucose |
| GHCA | Cystine | C12:0 | Valine | Insulin |
| HCA | Glycine | C14:0 | Phenylalanine | HDL |
| THCA | Histidine | C14:0 iso | | LDL |
| TLCA | Isoleucine | C14:1 n5 | | |
| HDCA | Leucine | C15:0 iso | | |
| HCA | Methionine | C15:0 | | |
| | N-Acetyl-L-asparticacid | C16:0 | | |
| | Proline | C16:0 iso | | |
| | Pyroglutamicacid | C16:1 n7 | | |
| | Serine | C16:1 t9 | | |
| | S-Methyl-cysteine | C17:0 iso | | |
| | Threonine | C17:0 | | |
| | Tryptophan | C18:0 | | |
| | Tyrosine | C18:0 iso | | |
| | Valine | C18:1 n9 | | |
| | Phenylalnine | C18:1 t9 | | |
| | | C18:2 n6 | | |
| | | C18:3 n3 | | |
| | | C19:0 | | |
| | | C19:1 n9 | | |
| | | C20:1 n9 | | |
| | | C20:3 n6 | | |
| | | C20:4 n6 | | |
| | | C22:1 n9 | | |
| | | C22:4 n-6 | | |

| Bile Acids | Amino Acids | Free Fatty Acids | Amino Acids | Blood biochemical Index biomarkers |
|---|---|---|---|---|
| GHDCA | Aspartic acid | C16:0/C18:0 | Isoleucine | TG |
| TCDCA | Beta-Alanine | C18:1 n9/C18:0 | Leucine | HBA1c |
| TDCA | Creatine | C20:3 n6/C20:4 | Tyrosine | Glucose |
| GHCA | Cystine | C12:0 | Valine | Insulin |
| HCA | Glycine | C14:0 | Phenylalanine | HDL |
| THCA | Histidine | C14:0 iso | | LDL |
| TLCA | Isoleucine | C14:1 n5 | | |
| HDCA | Leucine | C15:0 iso | | |
| HCA | Methionine | C15:0 | | |
| | N-Acetyl-L-asparticacid | C16:0 | | |
| | Proline | C16:0 iso | | |
| | Pyroglutamicacid | C16:1 n7 | | |
| | Serine | C16:1 t9 | | |
| | S-Methyl-cysteine | C17:0 iso | | |
| | Threonine | C17:0 | | |
| | Tryptophan | C18:0 | | |
| | Tyrosine | C18:0 iso | | |
| | Valine | C18:1 n9 | | |
| | Phenylalnine | C18:1 t9 | | |
| | | C18:2 n6 | | |
| | | C18:3 n3 | | |
| | | C19:0 | | |
| | | C19:1 n9 | | |
| | | C20:1 n9 | | |
| | | C20:3 n6 | | |
| | | C20:4 n6 | | |
| | | C22:1 n9 | | |
| | | C22:4 n-6 | | |

| Panel ID | GHDCA or %GHDCA | THDCA or %THDCA | HDCA or %HDCA | HCA or %HCA | GHCA or %GHCA | THCA or %THCA | Palmitic acid (C16:0) | Stearic acid (C18:0) | dihomo-γ-linolenic acid (C20:3 n6) | Arachidonic acid (C20:4 n6) | C16:0/C18:0 | C18:1 n9/C18:0 | C20:3 n6/C20:4 | Isoleucine | Leucine | Tyrosine | Valine | Phenylalanine | Triglycerides (TG) |
|---|---|---|---|---|---|---|---|---|---|---|---|---|---|---|---|---|---|---|---|
| A | x | | | | | | | | | | x | | | | | | | | |
| B | x | | | | | | | | | | | x | | | | | | | |
| C | x | | | | | | | | | | | | x | | | | | | |
| D | x | | | | | | | | | | x | x | | | | | | | |
| E | x | | | | | | | | | | x | | x | | | | | | |
| F | x | | | | | | | | | | | x | x | | | | | | |
| G | x | | | | | | | | | | x | x | x | | | | | | |
| H | x | | | | | | | | | | x | | | | | | | | x |
| I | x | | | | | | | | | | | x | | | | | | | x |
| J | x | | | | | | | | | | | | x | | | | | | x |
| K | x | | | | | | | | | | x | x | | | | | | | x |
| L | x | | | | | | | | | | x | | x | | | | | | x |
| M | x | | | | | | | | | | | x | x | | | | | | x |
| N | x | | | | | | | | | | x | x | x | | | | | | x |
| O | x | | | | | | | | | | x | x | x | x | x | x | x | x | x |
| P | x | | | | | | | | | | x | x | x | x | x | x | x | x | |
| Q | x | | | | | | x | x | x | x | | | | | | | | | |
| R | x | | | | | | x | x | x | x | | | | x | x | x | x | x | x |
| S | x | | | | | | | | | | | | | x | x | x | x | x | |
| T | | | | | | | x | x | x | x | | | | | | | | | |
| U | | | | | | | x | x | x | x | | | | | | | | | x |
| V | | | | | | | | | | | x | | | | | | | | |
| W | | | | | | | | | | | x | x | x | x | x | x | x | x | |
| X | | | | | | | | | | | x | x | x | x | x | x | x | x | x |
| Y | x | | | | | | x | x | x | x | | | | | | | | | x |
| Z | | | x | | | | | | | | x | | | | | | | | |
| AA | | | x | | | | | | | | | | x | | | | | | |

Fig. 12B

| Panel ID | GHDCA or %GHDCA | THDCA or %THDCA | HDCA or %HDCA | HCA or %HCA | GHCA or %GHCA | THCA or %THCA | Palmitic acid (C16:0) | Stearic acid (C18:0) | dihomo-γ-linolenic acid (C20:3 n6) | Arachidonic acid (C20:4 n6) | C16:0/C18:0 | C18:1 n9/C18:0 | C20:3 n6/C20:4 | Isoleucine | Leucine | Tyrosine | Valine | Phenylalanine | Triglycerides (TG) |
|---|---|---|---|---|---|---|---|---|---|---|---|---|---|---|---|---|---|---|---|
| AB | | | | | x | | | | | | | | x | | | | | | |
| AC | | | | | x | | | | | | x | x | | | | | | | |
| AD | | | | | x | | | | | | x | | x | | | | | | |
| AE | | | | | x | | | | | | | x | x | | | | | | |
| AF | | | | | x | | | | | | x | x | x | | | | | | |
| AG | | | | | x | | | | | | x | | | | | | | | x |
| AH | | | | | x | | | | | | | x | | | | | | | x |
| AI | | | | | x | | | | | | | | x | | | | | | x |
| AJ | | | | | x | | | | | | x | x | | | | | | | x |
| AK | | | | | x | | | | | | x | | x | | | | | | x |
| AL | | | | | x | | | | | | | x | x | | | | | | x |
| AM | | | | | x | | | | | | x | x | x | | | | | | x |
| AN | | | | | x | | | | | | x | x | x | x | x | x | x | x | x |
| AO | | | | | x | | | | | | x | x | x | x | x | x | x | x | |
| AP | | | | | x | | x | x | x | x | | | | | | | | | |
| AQ | | | | | x | | x | x | x | x | | | | x | x | x | x | x | |
| AR | | | | | x | | | | | | | | | x | x | x | x | x | |
| AS | | | x | x | | | | | | | | | | | | | | | |
| AT | x | x | x | x | | | | | | | | | | | | | | | |
| AU | x | x | x | x | x | x | | | | | | | | | | | | | |
| AV | | | x | x | | | | | | | x | | | | | | | | |
| AW | x | x | x | x | | | | | | | x | | | | | | | | |
| AX | x | x | x | x | x | x | | | | | x | | | | | | | | |
| AY | | | x | x | | | | | | | | x | | | | | | | |
| AZ | x | x | x | x | | | | | | | | x | | | | | | | |
| BA | x | x | x | x | x | x | | | | | | x | | | | | | | |
| BB | | | x | x | | | | | | | | x | | | | | | | |

Fig. 12C

| Panel ID | GHDCA or %GHDCA | THDCA or %THDCA | HDCA or %HDCA | HCA or %HCA | GHCA or %GHCA | THCA or %THCA | Palmitic acid (C16:0) | Stearic acid (C18:0) | dihomo-γ-linolenic acid (C20:3 n6) | Arachidonic acid (C20:4 n6) | C16:0/C18:0 | C18:1 n9/C18:0 | C20:3 n6/C20:4 | Isoleucine | Leucine | Tyrosine | Valine | Phenylalanine | Triglycerides (TG) |
|---|---|---|---|---|---|---|---|---|---|---|---|---|---|---|---|---|---|---|---|
| BC | x | x | x | x | | | | | | | | | x | | | | | | |
| BD | x | x | x | x | x | x | | | | | | | x | | | | | | |
| BE | | | | x | | | | | | | x | | | | | | | | |
| BF | | | x | x | | | | | | | x | | | | | | | | |
| BG | | | | x | | | | | | | | x | | | | | | | |
| BH | | | x | x | | | | | | | | x | | | | | | | |
| BI | | | | x | | | | | | | | | x | | | | | | |
| BJ | | | x | x | | | | | | | | | x | | | | | | |
| BK | x | | | x | | | | | | | x | | | | | | | | |
| BL | x | | | x | | | | | | | | x | | | | | | | |
| BM | x | | | x | | | | | | | | | x | | | | | | |
| BN | x | | | x | | | | | | | x | x | | | | | | | |
| BO | x | | | x | | | | | | | x | | x | | | | | | |
| BP | x | | | x | | | | | | | | x | x | | | | | | |
| BQ | | | | x | | | x | x | x | x | | | | | | | | | x |
| BR | x | | | x | | | x | x | x | x | | | | | | | | | x |
| BS | x | | x | x | | | | | | | x | | | | | | | | |
| BT | x | | x | x | | | | | | | | x | | | | | | | |
| BU | x | | x | x | | | | | | | | | x | | | | | | |
| BV | x | | | x | | | | | | | | | | | | | | | |
| BW | x | | x | x | | | | | | | | | | | | | | | |
| BX | x | x | x | x | x | x | | | | | | | | | | | | | x |
| BY | x | x | x | x | x | x | x | x | x | x | | | | | | | | | x |
| BZ | x | x | x | x | x | x | | | | | | | | x | x | x | x | x | x |

DIABETES-RELATED BIOMARKERS AND TREATMENT OF DIABETES-RELATED CONDITIONS

CROSS-REFERENCE TO RELATED APPLICATIONS

This application claims priority to U.S. provisional application No. 62/243,131 filed 18 Oct. 2015 which is hereby incorporated by reference.

TECHNICAL FIELD

The present invention relates to biomarkers associated with diabetes, methods of using the biomarkers to determine the risk that an individual will develop diabetes, and methods of screening a population to identify persons at risk for developing diabetes.

BACKGROUND

Diabetes is a serious illness characterized by a loss of the ability to regulate blood glucose levels. The World Health organization (WHO) estimates that more than 180 million people worldwide have diabetes. This number is likely to more than double by 2030. In 2005, an estimated 1.1 million people died from diabetes, this estimate likely undercounts deaths caused by diabetes, as diabetes contributes to other diseases, such as heart disease and kidney disease that may be listed as the cause of death. Almost 80% of diabetes deaths occur in low and middle-income countries. In China, the prevalence rate of diabetes is 9.7% in people over the age of 20, among which the rate is 10.6% for males and 8.8% for females. Based on this prevalence, the total number of diabetes is estimated to be 92.4 million, ranking the first in the world. Meanwhile, the prevalence rate of pre-diabetes is 15.5%, with an estimated number of 148 million.

Obesity, the result of chronic nutrient imbalance, is closely associated with the increased risk of type 2 diabetes (T2D). Even within the metabolically healthy (MH), adjusted diabetes risk has been reported to be 2-fold higher in overweight and 4-fold higher or 12-fold higher in obese compared with those normal weight (NW) individuals. Thus, the identification of early metabolic abnormalities can be used to recognize the higher risk overweight or obese (OW/OB) individuals and predict progression to T2D.

What is needed in the art is a biomarker or combination of biomarkers capable not only of identifying diabetes but also of determining the risk that an individual will develop diabetes.

SUMMARY OF THE INVENTION

The present invention relates to the identification of biomarkers associated with subjects having diabetes, pre-diabetes, or a pre-diabetic condition. The present invention provides biomarkers useful for evaluating the risk that a subject will develop diabetes, monitoring such risk, identifying members of a population at risk of developing diabetes, calculating risk of a subject developing diabetes, advising subjects of risk for developing diabetes, providing diagnostic tests for identifying subjects at risk for developing diabetes or kits there for, and providing diagnostic tests for determining risk of a subject developing diabetes and kits there for.

A first aspect of the invention provides a panel of biomarkers. A panel of biomarkers taught herein can be measured and used to evaluate the risk that a subject will develop diabetes ('diabetes risk') in the future, for example, the risk that an individual will develop diabetes in the next 1, 2, 5, or 10 years. The panel comprises a set of one or more biomarkers that can be employed for methods, kits, computer readable media, systems, and other aspects of the invention which employ a panel of biomarkers. The panel can comprise one or more biomarkers listed in FIG. 11. Optionally, the panel comprises a panel selected from panels A-BZ listed in FIG. 12A-12C.

A second aspect of the invention provides a diagnostic method. A diagnostic method of the invention comprises measuring, in a biological sample ('sample') obtained from a subject, the level of each biomarker of a panel taught herein, and evaluating the diabetes status of the subject based on the measured level.

Optionally, the diabetes status can include, for example, the risk of developing diabetes or a change in risk of developing diabetes. For example evaluating diabetes status can comprise, for example, evaluating diabetes risk or monitoring diabetes status (e.g. evaluating the change in diabetes risk).

Optionally, the step of evaluating can comprises correlating the measured level of each biomarker (e.g. individually or collectively) with diabetes risk. For example, correlating can comprise:
a. comparing the measured level of each biomarker of the panel to a comparator level (e.g. a level indicative of diabetes risk), and evaluating diabetes risk based on the comparison; or
b. evaluating diabetes risk based on an output from a model (e.g. algorithm), wherein the model is executed based on an input of the measured level of each biomarker of the panel.

Optionally, the step of evaluating diabetes risk comprises determining that the subject is at risk for developing diabetes. Optionally, the step of evaluating comprises calculating risk or likelihood of the subject developing diabetes (e.g. calculating a risk score).

Optionally, the subject is any of: a metabolically healthy subject, a subject that that has not been previously diagnosed as at risk for developing diabetes, a subject that that has not been previously diagnosed as having diabetes or pre-diabetes, and a subject that has undergone treatment that reduces diabetes or diabetes risk (e.g. metabolic surgery or a very low carbohydrate diet).

Optionally, the sample is blood, plasma, or serum.

Optionally, the method of measuring comprises mass spectrometry ('MS'). The MS can be performed following, for example, a separate technique such as gas chromatography ('GC') or liquid chromatography ('LC'). Optionally, the MS comprises GC-MS, LC-MS, or ultra-performance liquid chromatography-triple quadrupole mass spectrometry (UPLC-TQ).

A third aspect of the invention provides a method of treatment comprising administering or recommending (hereinafter individually and collectively referred to as 'administering') treatment to a subject that has been evaluated as at risk for developing diabetes by a diagnostic method according to the invention, a treatment that delays or prevents the onset of diabetes.

Optionally, the treatment is any standard of care for a subject having diabetes.

Optionally, the treatment is a treatment that reduces the deviation between the level of one or more biomarkers of the panel exhibited by the subject and a comparator level that is indicative of reduced diabetes risk.

Optionally, the treatment comprises metabolic surgery, a very low carbohydrate diet ('VLCD'), carbohydrate restriction, or calorie restriction.

Optionally, the treatment comprises an anti-diabetic agent.

Optionally, the method further comprises, following administering the treatment, measuring, the level of each biomarker of the panel in a sample obtained from the subject post-treatment, and comparing the post-treatment level to the pre-treatment level, and evaluating whether the treatment has reduced the diabetes risk of the subject. Optionally, the method further comprises modifying the treatment following a determination that the diabetes risk has not been reduced by the treatment.

A fourth aspect of the invention provides a kit comprising one or more reagents for detecting a panel of one or more biomarkers taught herein. The one or more reagents comprise one or more internal standards, wherein, collectively, the one or more internal standards provide at least one internal standard for each biomarker of the panel. Optionally, the kit comprises a mixture of said internal standards (e.g. a mixture thereof). Optionally, the one or more or more internal standards are lyophilized. Optionally, one or more reagents are provided in a container.

In any aspect of the invention, the panel optionally comprises one or more bile acids, one or more amino acids, one or more free fatty acids, and/or one or more one or more blood biochemical index biomarkers.

Optionally, the one or more bile acids are selected from Glycohyodeoxycholic acid ('GHDCA'), Taurohyodeoxycholic acid ('THDCA'), Hyodeoxycholic acid ('HDCA'), Taurochenodeoxycholic acid ('TCDCA'), Taurodeoxycholic acid ('TDCA'), Glycohyocholic acid ('GHCA'), Hyocholic acid ('HCA'), Taurohyocholic acid ('THCA'), and Taurolithocholic acid ('TLCA').

Optionally, the one or more one or more amino acids comprise one or more branch chain amino acids ('BCAAs') and/or one or more aromatic amino acids ('AAAs'). Optionally, the BCAAs comprises one or more of leucine, isoleucine, and valine. Optionally, the AAAs comprises phenylalanine and/or tyrosine.

Optionally, the one or more one or more amino acids comprise one or more of Alanine, Aspartic acid, Beta-Alanine, Creatine, Cystine, Glycine, Histidine, Isoleucine, Leucine, Methionine, N-Acetyl-L-aspartic acid, Proline, Pyroglutamic acid, Serine, S-Methyl-cysteine, Threonine, Tryptophan, Tyrosine, Valine, and Phenylalnine.

Optionally, the one or more one or more free fatty acids comprises one or more of Lauric acid (C12:0), Myristic acid (C14:0), 12-Methyltridecanoic acid (C14:0 iso), Myristoleic acid (C14:1 n5), 13-Methylmyristic acid (C15:0 iso), Pentadecanoic acid (C15:0), Palmitic acid (C16:0), 14-methylpentadecanoic acid (C16:0 iso), Palmitoleic acid (C16:1 n7), Palmitelaidic acid (C16:1 t9), 15-Methylpalmitic acid (C17:0 iso), Margaric acid (C17:0), Stearic acid (C18:0), 16-Methylmargaric acid (C18:0 iso), Oleic acid (C18:1 n9), Elaidic acid (C18:1 t9), Linoleic acid (C18:2 n6), α-Linolenic acid (C18:3 n3), Nonadecanoic acid (C19:0), Nonadecenoic acid (C19:1 n9), Eicosenoic acid (C20:1 n9), dihomo-γ-linolenic acid (C20:3 n6), Arachidonic acid (C20:4 n6), Erucic acid (C22:1 n9), Docosatetraenoic acid (C22:4 n-6), Docosapentaenoic acid (C22:5 n-6), and Eicosenoic acid (C20:1 n-9).

Optionally, the one or more blood biochemical index biomarkers comprise one or more of total Triglycerides (TG), Gemoglobin A1c (HBA1c), Glucose, Insulin, High density lipoprotein (HDL), and Low density lipoprotein (LDL).

Optionally, the panel comprises:
a. one or more (e.g. each) of GHDCA or % GHDCA of total bile acids, THDCA or % THDCA, HDCA or % HDCA of total bile acids, HCA or % HCA of total bile acids, GHCA or % GHCA, and THCA or % THCA;
b. one or more (e.g. each) of Palmitic acid (C16:0), Stearic acid (C18:0), Oleic acid (C18:1 n9), dihomo-γ-linolenic acid (C20:3 n6), and Arachidonic acid (C20:4 n6);
c. one or more (e.g. each) of Isoleucine, Leucine, Tyrosine, Valine, and Phenylalanine;
d. TG;
e. a combination of (a) and (b), (a) and (c), (a) and (d), (b) and (c), (b) and (d), or (c) and (d);
f. a combination (a), (b), and (c);
g. a combination (a), (b), and (d);
h. a combination (a), (c), and (d); or
i. a combination (b), (c), and (d).

BRIEF DESCRIPTION OF THE DRAWINGS

FIG. 11 depicts biomarkers useful in the present invention.

FIGS. 12A-12C depict biomarker panels useful in the present invention. The biomarker panels are identified as panels A through BZ.

DETAILED DESCRIPTION OF THE INVENTION

Methods

Overview

Figure 1:
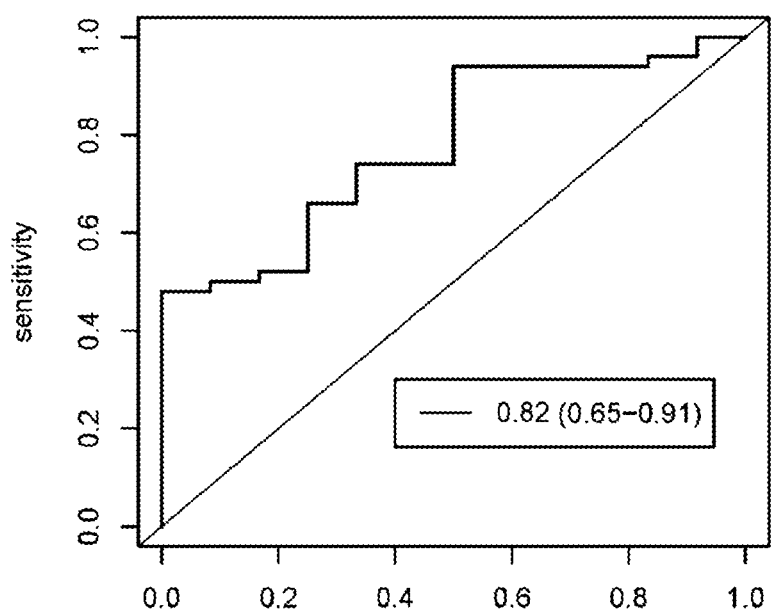
FIG. 1 depicts an ROC curve useful in carrying out a method of the invention.

One embodiment of the invention provides a diagnostic method comprising evaluating diabetes status (e.g. diabetes risk) in a subject. Diabetes risk can optionally be evaluated by measuring, in a sample obtained from the subject, the level of one or more biomarkers of a panel taught herein and correlating the measured level of the level of one or more biomarkers with diabetes risk. Based on the correlation, the invention can evaluate subjects as having an increased risk of developing diabetes, thereby identifying subjects having an increased risk of developing diabetes.

Optionally, subjects identified as having an increased risk of developing diabetes and are selected to receive treatment to delay or prevent the onset of diabetes, or reduce diabetes risk.

Optionally, the method comprises monitoring the level of the one or more biomarker of the panel. Methods of monitoring can comprise providing a first biological sample can be provided from the subject at a first time (e.g. prior to undergoing treatment) and a second biological sample can be provided from the subject at a later time (e.g. following the treatment), and measuring the level of the one or more biomarkers in the first sample and second sample.

Subject

Methods of the invention can measure the level of one or more biomarkers in a biological sample obtained from a subject. The subject can be any subject, e.g. a human subject.

The invention is surprisingly useful for correlating diabetes risk in a subject when implemented with subjects that do or do not exhibit typical phenotypes of diabetes or diabetes risk.

Optionally, the subject is a metabolically healthy subject.

Optionally, the subject is any of: a metabolically healthy subject, a subject that that has not been previously diagnosed as at risk for developing diabetes, a subject that that has not been previously diagnosed as having diabetes or pre-diabetes, and a subject that has undergone treatment that reduces diabetes or diabetes risk (e.g. metabolic surgery or a very low carbohydrate diet).

Optionally, the subject is a metabolically healthy. For example, the subject optionally exhibits one or more or each of the following: FPG ≤6.1 mmol/L, OGTT ≤7.8 mmol/L, SBP/DBP <140/90 mmHg, fasting plasma TG <1.7 mmol, fasting plasma HDL≥0.9 mmol/L (for men) or ≥1.0 mmol/L (for women). Optionally, the subject has no previous history of high cholesterol (TC <5.18 mmol/L); no cardiovascular or endocrine disease history, has not been previously diagnosed with diabetes, and/or has no previous history of high blood pressure.

Optionally, the subject exhibits one or more (e.g. each) of low fasting blood glucose, insulin, or HBA1c levels. For example, the subject can exhibit ≤10 mU/mL fasting insulin level, less than 6% fasting HBA1c level, and/or ≤126 mg/dl fasting glucose level.

Optionally, the subject does not exhibit hypertension, e.g. consistent (e.g. repeated measurements over time of) blood pressure above 140/90.

Optionally, the subject does not exhibit an LDL cholesterol level above 137 and/or total cholesterol level above 200.

Optionally, the subject is a non-obese subject. For example, the subject can have a BMI of less than 30, less than 29, or less than 25.

Optionally, the subject is not overweight. For example, the subject can have a BMI of less than 24.

Optionally, the subject is overweight. For example, the subject can have a BMI of at least 24.

Optionally, the subject a non-morbidly obese subject. For example, the subject can have a BMI of less than 35.

Optionally, the subject is a woman having a fat percentage of ≤30% for women or a man having a body fat percentage of ≤25%.

Optionally, the subject has a BMI of at least 24 or at least 28 and the subject exhibits FPG ≤6.1 mmol/L, OGTT ≤7.8 mmol/L, SBP/DBP <140/90 mmHg, fasting plasma TG <1.7 mmol, fasting plasma HDL≥0.9 mmol/L (for men) or ≥1.0 mmol/L (for women).

Optionally, the subject has a BMI of less than 28 or less than 24 and the subject exhibits FPG ≤6.1 mmol/L, OGTT ≤7.8 mmol/L, SBP/DBP <140/90 mmHg, fasting plasma TG <1.7 mmol, fasting plasma HDL≥0.9 mmol/L (for men) or ≥1.0 mmol/L (for women).

Sample

Methods of the invention can measure the level of one or more biomarkers in a biological sample ('sample') obtained from a subject.

Optionally, the sample comprises blood, plasma, or serum. For example, any of such samples can be obtained from a subject following a period of fasting. The collection of fasting samples is well-known in the art.

Optionally, the sample comprises or consists of serum. As used herein, "serum" refers to the fluid portion of the blood obtained after the removal of the fibrin clot and blood cells, distinguished from the plasma in circulating blood.

Internal Standards

Methods of the invention optionally comprise the use of an internal standard for one or more (e.g. each) of the biomarkers that are measured. An internal standard can optionally be mixed with the sample at any time prior to measurement.

Optionally, the internal standard, having a known initial level in the sample prior to sample preparation, can provide a measurement signal used to normalize the signal of the respective biomarker.

Steps of sample preparation can sometimes induce substantial loss of biomarker prior to measurement. While the development of a predictable sample preparation technique and use of the same separation and measurement instruments (e.g. the same LCMS machine) can increase accuracy and precision of measurement, the use of different sample preparation mediums, methods, and measurement machines can induce unpredictable changes in biomarker recovery and/or measurement signal. Accordingly, an internal standard can optionally be used in the present invention to correct for loss (i.e. recovery inconsistencies) and/or signal level variation of a respective biomarker during sample preparation and measurement. For example, an internal standard can be added to the sample after sample collection but before sample preparation for measurement (e.g. before filtering, extraction, and/or precipitation steps).

Optionally, the internal standards are configured for GC-MS or LC-MS.

Optionally, an internal standard is provided that is the same compound as a corresponding biomarker of the panel, except it has one or more of its atoms replaced with a stable isotope of the one or more atoms (e.g. $(2)H$, $(13)C$, $(15)N$, or $(18)O$). For example, a set of internal standards for a given panel of biomarkers can be provided by providing an isotope labeled variant of each biomarker of the panel.

Optionally, an internal standard compound is chemically similar, but not identical to the respective one or more biomarkers that are measured such that the internal standard exhibits similar behavior during sample preparation but can be uniquely identified during the measurement step. Optionally, the internal standard is selected such that effects of sample preparation on the measurement signal level of internal standard should be the same relative to the measurement signal level of the respective biomarker.

Optionally, the internal standard is mixed with the sample prior to one or more steps of preparation (e.g. extraction or other purification), and biomarker separation steps.

Optionally, the panel comprises a plurality of biomarkers and a different internal standard for each biomarker (e.g. a labeled biomarker identical to the respective biomarker other than the label). Alternatively, at least one internal standard is provided for normalization of a plurality of biomarkers (e.g. a biomarker of the same compound class one or more respective biomarkers such as a labeled steroid acid or bile acid for a plurality of bile acids, a labeled fatty acid for a plurality of fatty acid biomarkers, and/or a labeled amino acid for a plurality of amino acids). For example, nonadecanoic-d37 acid can optionally be provided as an internal standard for all of the free fatty acids of a panel taught herein.

Optionally, the internal standard is an isotope labeled compound.

Alternatively, the internal standard is any compound not found in the sample, e.g. not found in blood, plasma, or serum.

Optionally, the internal standard is a stable isotope labeled compound (e.g. labeled variant of the biomarker or labeled variant of a compound with similar properties as the biomarker). Optionally, the stable isotope is $(2)H$, $(13)C$, $(15)N$, or $(18)O$.

Optionally, one or more internal standards are selected from a labeled steroid acid such as a bile acid (e.g. used for a bile acid biomarker), a labeled fatty acid (e.g. used for a fatty acid biomarker) and/or a labeled amino acid (e.g. used for an amino acid biomarker).

Optionally, useful internal standards are any stable-isotope labeled variants of respective biomarkers to be determined in the samples. Optionally, the internal standards have the same chemical properties as the metabolite biomarkers to be measured from the panel. For example, with respect to a corresponding biomarker of the panel, the internal standard can be selected such that it produces the same recovery percent when extracted by protein precipitation (e.g. by Ammonium sulfate, trichloroacetic acid (TCA), acetone, or ethanol) and/or filtration (e.g. using filters taught herein) from the sample. Given a particular biomarker panel, the skilled artisan can readily select internal standards that have the same or shared chemical properties as a corresponding biomarker, wherein the same or shared chemical properties are those that influence the recovery percentage of a biomarker and internal standard (e.g. molecular weight, polarity, shared R-groups, etc.). Optionally, the recovery rate of each internal standard is substantially the same as the respective biomarker, for example, less than 10%, 7%, 5%, 4%, 3%, 2%, 1%, or 0.5% difference in recovery rate relative to the corresponding biomarker.

For example, the following illustrate useful internal standards of corresponding biomarkers measurement in the present invention:

cholic acid (CA)-d4 (e.g. used for hyocholic acid (HCA'));

ursodeoxycholic acid (UDCA)-d4 (e.g. used for glycohyodeoxycholic acid (GHDCA), taurochenodeoxycholic acid (TCDCA), taurodeoxycholic acid ('TDCA'), glycohyocholic acid ('GHCA'), and/or taurohyocholic acid ('THCA'));

lithocholic acid (LCA)-d4 (e.g. used for taurolithocholic acid ('TLCA'));

tridecanoic-d25 acid (e.g. used for monounsaturated free fatty acids);

nonadecanoic-d37 acid (e.g. used for saturated free fatty acids);

Valine-d8 (used for valine);

Leucine-5,5,5-d3 (used for leucine);

Isoleucine-2-d1 (used for isoleucine);

Tyrosine-3,3-d2 (used for tyrosine); and

Phenylalanine-3,3-d2 (used for phenylalanine)

With the teachings provided herein, the skilled artisan can readily select useful internal standards based on the selection of a biomarker panel.

Sample Preparation

The biomarkers measured in the present invention can optionally be extracted from a sample obtained from a subject. For example, the method optionally comprises steps of contacting the sample with an extraction medium, extracting the biomarkers from the sample, and measuring the extracted lipids (e.g. by mass spectrometry following separation of the biomarkers by chromatography).

The extraction medium can be any medium that allows the extraction of biomarkers from one or more other components of the sample that are not measured in the measuring step. Optionally, the extraction medium comprises a solution (e.g. protein precipitating solution), a filter, or both.

Measurement

Methods of the invention optionally measure the level of one or more biomarkers that are present in a biological sample. The step of measuring can be performed in any manner useful to measure the biomarkers taught herein.

Optionally, the method of measuring comprises mass spectrometry ('MS').

The MS can be performed following, for example, a separate technique such as gas chromatography ('GC') or liquid chromatography ('LC'). Optionally, the MS comprises GC-MS, LC-MS, or ultra-performance liquid chromatography-triple quadrupole mass spectrometry (UPLC-TQ).

Optionally, the step of measurement is preceded by steps of extraction (e.g. filtration) and/or separation (e.g. chromatography). Chromatography is a method of separating components in a sample based on differences in partitioning behavior between a mobile phase and a stationary phase. Typically, a column holds the stationary phase and the mobile phase carries the sample through the column. Sample components that partition strongly into the stationary phase spend a greater amount of time in the column and are separated from components that stay predominantly in the mobile phase and pass through the column faster. As the components elute from the column, they can be measured, e.g. using a mass spectrometer.

Optionally, each of the biomarkers of a panel taught herein is measured from the same aliquot of the sample following instruction of the aliquot in a chromatography column. Such an embodiment can separate all of the biomarkers from a single aliquot and provides an efficient method by eliminating the need for parallel sample preparation, extraction, and separation steps.

Such a simultaneous running of all biomarkers can be provided by tailoring the chromatographic conditions, e.g. the column temperature, the composition of mobile phase, flow rate, eluent condition of mobile phase, analytical time as well as the mass fragmentation pattern (parent ion and daughter ion of the biomarker to be measured) of metabolites to get adequate separation.

When the biomarker of interest is an analyte (e.g. palmitic acid or stearic acid), the step of "measuring" can include measuring the level (e.g. measuring a signal indicative of the level) of the analyte. When biomarker of interest is a calculation based on of a plurality of analytes such as ratio (e.g. P/S ratio), percentage (e.g. % GHDCA of total bile acids), or sum (e.g. TG, total triglycerides), the step of measuring can include measuring the levels of each of the plurality of analytes and calculating the level of the biomarker based on the measured levels.

The term "level", as used herein with respect to a biomarker, can be any quantitative or qualitative representation of the presence of the biomarker in the sample, e.g. the amount (e.g. mass) or concentration (e.g. w/w, w/v, or molarity).

When expressed as a concentration, the level can be expressed with respect to the volume (or weight) of the obtained sample prior to sample preparation (e.g. extraction).

Correlation

According to a method of the invention, evaluating diabetes status can optionally comprise correlating the measured level of one or more biomarkers of the panel with diabetes risk. Based on the correlation, the risk of developing diabetes (e.g. likelihood of developing diabetes) can optionally be determined. For example, it can be determined whether the subject is likely (e.g. whether likelihood is greater than a preset likelihood threshold) to develop diabetes or has a high risk (e.g. greater than a risk threshold) for developing diabetes. Such subjects are sometimes referred to herein as being at risk for developing diabetes. Subjects determined to be at risk can optionally be identified and/or selected, e.g. to receive advice and/or treatment.

Optionally, the step of correlating comprises comparing one or more measured biomarker levels to respective comparator levels (e.g. a level indicative of low risk or no risk, or a threshold level that distinguishes risk levels). Additionally or alternatively, measured levels of one or a plurality of biomarkers can be inputted into a model (e.g. mathematical formula or algorithm) that computes a single score based on the measured levels. Such as score can itself be correlated with risk of developing diabetes (e.g. where the score is compared to a threshold score indicative of a clinical endpoint such as the development of diabetes within a time period).

A biomarker level (e.g. measured level) or a score (e.g. computed by model) can be compared to a comparator level or comparator score, respectfully, utilizing techniques such as reference limits, discrimination limits, or risk defining thresholds to define cutoff points and abnormal values for a state such as diabetes risk. The comparator level of a biomarker or combined biomarker score can be, for example, a level or score, respectively, typically found in a subject not at risk for developing diabetes or at low risk for developing diabetes (or conversely a subject at risk or at high risk). The risk can go up or down, depending on whether a subject's measured level or score is greater or lower than the comparator level or score (e.g. noting that, with respect to Table 3, all biomarkers, other than GHDCA and % GHDCA, were increased in subjects that later developed diabetes and GHDCA and % GHDCA were decreased in subjects that later developed diabetes). Such comparator levels and cutoff points may optionally vary based on whether a biomarker is used alone or in a formula combining with other biomarkers into a score. Alternatively, a comparator level or score can be determined from previously tested subjects who did not develop diabetes over a clinically relevant time horizon (e.g. 1, 2, 5, or 10 years), or a threshold that was determined to distinguish subjects who developed diabetes from subjects who did not did not develop diabetes over a clinically relevant time horizon (e.g. as taught in the Examples). Optionally, the comparator level or comparator score is the level or score, respectively, that distinguishes between high risk and low risk subjects. A high risk score or likely diabetes development can be defined at-will by the clinician, and can indicate for example, at least 70% risk (e.g. wherein 70% of the subjects studied that had a level or score at or above the comparator developed diabetes over the time horizon), at least 75% risk, at least 80% risk, at least 85% risk, at least 90% risk, at least 85% risk, at least 90% risk, or at least 95%. Additionally or alternatively, several risk classifications (e.g. very low, low, medium, high, and very high) can be provided, wherein each classification is identified by a given level or score range. Additionally or alternatively, an equation (e.g. curve) can be provided that correlates level or score to risk (e.g. relative or absolute) or likelihood (e.g. percent likelihood) of developing diabetes.

Optionally, a profile is provided comprising each of the measured or calculated levels of the one or more biomarkers of a panel and the measured profile is compared to a comparator biomarker profile. The biomarkers of the present invention can be used to generate a comparator biomarker profile. A comparator biomarker profile can be a low risk or no risk comparator, e.g. taken from subjects who did not develop diabetes or who rarely developed diabetes within a clinically significant time period following obtainment of the sample that exhibited the biomarker profile. Alternatively, a comparator profile can be a high risk comparator, e.g. taken from subjects that developed diabetes or who usually developed diabetes following the clinically significant time period following obtainment of the sample that exhibited the biomarkers. Optionally, the high risk comparator profile can be compared to the low risk profile to identify subjects at risk for developing diabetes, to monitor the progression of disease, to monitor the progression of diabetes risk, or to monitor the effectiveness of treatment. Optionally, the high risk comparator profile and/or low risk comparator profile can be stored on a non-volatile memory.

Optionally, a method of the invention uses a model (e.g. algorithm) to correlate measured biomarkers levels with diabetes risk. Such correlation using a model can be performed on a system configured there for, e.g. a computer having a program that implements the model and calculates a score based on the input of measured marker levels. Optionally, measurements of a biomarker panel of the present invention serve as inputs to a computer or microprocessor programmed with a model that implements an algorithm that computes a risk score. If some factors (e.g. physiological factors such as BMI, age, and sex) in addition to the biomarkers tested in the system are used to calculate the final risk score, then these factors can be supplied to the model so that it can complete the risk score calculation, or the algorithm can produce a preliminary score that will reported and externally combined with the other factors to calculate a final risk score.

The diabetes for which risk of development is evaluated can optionally be any diabetic condition and can be identified by any endpoint exhibited by subjects having a diabetic condition. The diabetes endpoint can include, for example, a two-hour glucose levels of at least 140 (e.g. 140- to 199 mg/dL, sometimes used as an endpoint for pre-diabetes) or at least 200 mg/dl (sometimes used as an endpoint for classical diabetes). Additionally or alternatively, the diabetes endpoint can include a glycated hemoglobin (HbA1c) level of at least 5.7% (e.g. 5.7% and 6.4%, sometimes used as an endpoint for pre-diabetes) or of at least 6.5% (sometimes used as an endpoint for classical diabetes). The diabetes can be, for example, non-insulin dependent diabetes, and can be pre-diabetes or classical diabetes. Alternatively, any other endpoint can be used to classify diabetes, e.g. Metabolic Syndrome ("Syndrome X"), Impaired Glucose Tolerance (IGT), and Impaired Fasting Glycemia (IFG). IGT refers to post-prandial abnormalities of glucose regulation, while IFG refers to abnormalities that are measured in a fasting state. The World Health Organization defines values for IFG as a fasting plasma glucose concentration of 6.1 mmol/L (100 mg/dL) or greater (whole blood 5.6 mmol/L; 100 mg/dL), but less than 7.0 mmol/L (126 mg/dL) (whole blood 6.1 mmol/L; 110 mg/dL). Metabolic syndrome according to the National Cholesterol Education Program (NCEP) criteria is defined as having at least three of the following: blood pressure greater than or equal to 130/85 mm Hg; fasting plasma glucose greater than or equal to 6.1 mmol/L; waist circumference >102 cm (men) or >88 cm (women); triglycerides greater than or equal to 1.7 mmol/L; and HDL cholesterol <1.0 mmol/L (men) or 1.3 mmol/L (women). Many individuals with pre-diabetic conditions will not convert to type 2 diabetes ('T2DM'). "Impaired glucose tolerance" (IGT) is a pre-diabetic condition defined as having a blood glucose level that is higher than normal, but not high enough to be classified as Diabetes Mellitus. A subject with IGT will have two-hour glucose levels of 140 to 199 mg/dL (7.8 to 11.0 mmol) on the 75-g oral glucose tolerance test. These glucose levels are above normal but below the level that is diagnostic for Diabetes. Subjects with impaired glucose tolerance or impaired fasting glucose have a significant risk of developing Diabetes and thus are an important target group for primary prevention. While these endpoints are well-known endpoints of clinical diagnosis, the skilled artisan will appreciate that such endpoints can be varied and produce a diabetes endpoint useful according to the invention. Further, other endpoints that are informative of diabetes or insulin resistance can also be used. Such endpoints can optionally be used to train a comparator profile score based on historical subjects that did or did not develop diabetes, and this comparator profile score can be used to compare against a subject that wishes to have his diabetes risk evaluated.

"Risk" in the context of the present invention, includes the probability that an event will occur over a specific time period, e.g., as in the conversion to frank type 2 diabetes, and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(1−p) where p is the probability of event and (1−p) is the probability of no event) to no-conversion. Alternative continuous measures which may be assessed in the context of the present invention include time to diabetes conversion and therapeutic diabetes conversion risk reduction ratios.

"Risk evaluation", in the context of the present invention encompasses making a prediction of the probability, odds, or likelihood that an event or disease state may occur, the rate of occurrence of the event or conversion from one disease state to another, i.e., from a normoglycemic condition to a pre-diabetic condition or pre-diabetes, or from a pre-diabetic condition to pre-diabetes or diabetes. Risk evaluation can also comprise prediction of future glucose, HBA1c scores or other indices of diabetes, either in absolute or relative terms in reference to a previously measured population. The methods of the present invention can optionally be used to make continuous or categorical measurements of the risk of conversion to Type 2 Diabetes, thus diagnosing and defining the risk spectrum of a category of subjects defined as pre-diabetic. In the categorical scenario, the invention can be used to discriminate between normal and pre-diabetes subject cohorts. In other embodiments, the present invention may be used so as to discriminate pre-diabetes from diabetes, or diabetes from normal. Such differing use may optionally require different biomarker combinations in individual panels, mathematical algorithm, and/or cut-off points, but be subject to the same aforementioned measurements of accuracy for the intended use.

In one embodiment, evaluation of diabetes risk comprises calculating a risk score. While certain scoring methods of the invention are exemplified using Logistic Regression-based correlation (e.g. as detailed in the Examples), the invention contemplates any method of correlation. For example, after selection of a set of biomarkers as disclosed in the instant invention, well-known techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), related decision tree classification techniques, Shrunken Centroids (SC), StepAIC, Kth-Nearest Neighbor, Boosting, Decision Trees, Neural Networks, Bayesian Networks, Support Vector Machines, and Hidden Markov Models, Linear Regression or classification algorithms, Nonlinear Regression or classification algorithms, analysis of variants (ANOVA), hierarchical analysis or clustering algorithms; hierarchical algorithms using decision trees; kernel based machine algorithms such as kernel partial least squares algorithms, kernel matching pursuit algorithms, kernel Fisher's discriminate analysis algorithms, or kernel principal components analysis algorithms, or other mathematical and statistical methods can be used to develop an algorithm for calculation of Diabetes risk score. Generally, a selected population of individuals is used, where historical information is available regarding the values of biomarkers in the population and their clinical outcomes such as the development of diabetes (e.g. as detailed in the Examples). To calculate a diabetes risk score for a given individual, biomarker values can optionally be obtained from one or more samples collected from the individual and used as input data, i.e. input into a model fitted (e.g. algorithm) to the actual historical data obtained from the selected population of individuals.

The performance and thus absolute and relative clinical usefulness of the invention may be assessed in multiple ways as noted above. Amongst the various assessments of performance, the invention is intended to provide accuracy in prediction of diabetes risk and treatment monitoring. Accuracy concerns the ability of the test, assay, or method to distinguish between subjects that will or will not develop diabetes, and is based on whether the subjects have an effective level or a substantial alteration in the level of one or more biomarkers, or a score calculated there from. By effective level or substantial alteration it is meant that the measurement of the biomarker is different than the predetermined cut-off point (or threshold value) for that biomarker or change in the level there of, respectively, and therefore indicates that the subject is at risk for developing diabetes or has undergone a change in diabetes risk (e.g. in methods of monitoring). The difference in the level of biomarker between at risk (or high risk) and not at risk (or low risk) is preferably statistically significant and may be an increase in biomarker level or a decrease in biomarker level, as is readily apparent from the Examples taught herein. While the invention contemplates the use of a one-biomarker panel, for some populations (e.g. exhibiting a specific genetic, physiological, or clinical state), achieving statistical significance, and thus the preferred analytical and clinical accuracy, many include combinations of several biomarkers to be used together in a panels and combined with mathematical models (e.g. algorithm) in order to achieve a statistically significant risk score.

As with the categorical diagnosis of a disease state, changing the cut point or threshold value of a test for diabetes risk according to the present invention may change the sensitivity and specificity, but often in a qualitatively inverse relationship. Therefore, in assessing the accuracy and usefulness of a proposed method, a test designer may optionally take both sensitivity and specificity into account and be mindful of what the cut point is at which the sensitivity and specificity are being reported because sensitivity and specificity may vary significantly over the range of cut points. Use of statistics such as AUC, encompassing all potential cut point values, is sometimes preferred for risk evaluation using the invention.

Using such statistics, an acceptable degree of diagnostic accuracy using a method of the invention to evaluate diabetes risk in which the AUC (area under the ROC curve for the test or assay) is optionally at least 0.60, or greater such as at least 0.65, at least 0.70, at least 0.75, at least 0.80, or at least 0.85. Optionally, the AUC is even greater, e.g. 0.875, at least 0.90, or at least 0.95.

Optionally, by defining the degree of diagnostic accuracy, i.e., cut points on a ROC curve, defining an acceptable AUC value, and determining the acceptable ranges in relative concentration of what constitutes a level (or score) of the biomarkers (individually or collectively) that distinguishes at-risk subjects from low risk subjects, the invention allows one of skill in the art to use the biomarkers to identify subjects that are at risk for developing diabetes with a high level of predictability and performance.

Models can also be developed and/or used as detailed below.

Development of a Scoring Model

While the Examples taught herein provide details of the development of a model for carrying out the invention, the skilled artisan will appreciate that, using the biomarkers identified herein and the relationships taught herein, a mathematical model used to calculate a score can be produced in any manner, and need not rely on the data collected and presented herein.

For example, the model can be produced by obtaining biomarker level data from a representative population including data from those who did and did not develop diabetes over a clinically significant time following biomarker level measurement (e.g. as detailed in the Examples). Such data can be obtained from the teachings provided herein (e.g. biomarker data detailed in the Examples), firsthand from the population, prospective (longitudinal) studies to involving observations of the representative population over a period of time, retrospective studies of samples of a representative population that queries the samples and/or from a retrospective epidemiological data storage containing the results from previous studies, such as an NIH database. The biomarker data may be derived from a single study or multiple studies, and generally include data pertaining to the desired indication and endpoint of the representative population, including values of the biomarkers described herein, clinical annotations (which may include endpoints), and most particularly the desired endpoints for training an algorithm for use in the invention, across many subjects. The biomarker level data is then optionally stored on nonvolatile memory.

The representative population data set can then be prepared as needed to meet the requirements of the model or analysis that will be used for biomarker selection, as described below. For example, data set preparation may include preparing the biomarker level values from each subject within the representative population, or a chosen subset thereof. However, the raw biomarker level data alone may not be entirely useful for the purposes of model training. As such, various data preparation methods may be used to prepare the data, such as gap fill techniques (e.g., nearest neighbor interpolation or other pattern recognition), quality checks, data combination using of various formulae (e.g., statistical classification algorithms), normalization and/or transformations, such as logarithmic functions to change the distribution of data to meet model requirements (e.g., base 10, natural log, etc.). Again, the particular data preparation procedures are dependent upon the model or models that will be trained using the representative population data. The particular data preparation techniques for various different model types are known, and need not be described further.

The particular biomarkers are optionally selected to be subsequently used in the training of the model used to evaluate a risk of developing a diabetic condition. Biomarker selection may involve utilizing a selection model to validate the representative population data set and selecting the biomarker data from the data set that provides the most reproducible results. Examples of data set validation may include, but are not limited to, cross-validation and bootstrapping. From the biomarker selection, the model to be used in evaluating a risk of developing a diabetic condition may be determined and selected. However, it is noted that not all models provide the same results with the same data set. For example, different models may utilize different numbers of biomarkers and produce different results, thereby adding significance to the combination of biomarkers on the selected model. Accordingly, multiple selection models may be chosen and utilized with the representative population data set, or subsets of the data set, in order to identify the optimal model for risk evaluation. Examples of the particular models, including statistical models, algorithms, etc., which may be used for selecting the biomarkers have been described above.

For each selection model used with the data set, or subset thereof, the biomarkers are optionally selected based on each biomarker's statistical significance in the model. When input into each model, the biomarkers are optionally selected based on various criteria for statistical significance, and may further involve cumulative voting and weighting. Tests for statistical significance may include exit-tests and analysis of variance (ANOVA). The model may include classification models (e.g., LDA, logistic regression, SVM, RF, tree models, etc.) and survival models (e.g., cox), many examples of which have been described above.

It is noted that while biomarkers may be applied individually to each selection model to identify the statistically significant biomarkers, in some instances individual biomarkers alone may provide less predictive power than desired, in which case combinations of biomarkers may be applied to the selection model. For example, rather than utilizing univariate biomarker selection, multivariate biomarker selection may be utilized. That is, a biomarker may not be a as good of an indicator when used as a univariate input to the selection model, relative to when it is used in combination with other biomarkers (e.g., a multivariate input to the model), because each marker may bring additional information to the combination that would not be indicative if taken alone.

The model to be used for evaluating risk is selected, trained and validated. In particular, leading candidate models may be selected based on one or more performance criteria, examples of which have been described above. For example, from using the data set, or data subsets, with various models, not only are the models used to determine statistically significant biomarkers, but the results may be used to select the optimal models along with the biomarkers. As such, the evaluation model used to evaluate risk may include one of those used as a selection model, including classification models and survival models. Combinations of models markers, including marker subsets, may be compared and validated in subsets and individual data sets. The comparison and validation may be repeated many times to train and validate the model and to choose an appropriate model, which is then used as a model for evaluating risk of a developing diabetes.

Use of a Scoring Model

While the Examples taught herein provide models for carrying out the invention, the skilled artisan will appreciate that, using the biomarkers identified herein and the relationships taught herein, any mathematical model using the biomarker panels taught herein can optionally be used to evaluate diabetes risk.

For example, a mathematical model is provided that can calculate a risk score based on an input of one or more biomarkers of a panel taught herein. Biomarker level data is obtained from a subject and optionally stored on non-volatile memory). The subject biomarker data may be initially derived through a variety of means, including self-reports, physical examination, laboratory testing and existing medical records, charts or databases. The subject biomarker level may be prepared using calculations, transforms, logs, combinations, normalization, etc. as needed according to the model type selected and trained (e.g. as detailed in the methods of developing a scoring model taught herein). Once the data has been prepared, the subject biomarker data can be input into the model. The model can then outputs a risk score (e.g. wherein the risk score is indicative of likelihood to develop diabetes, relative risk, or predicted time to diabetes contraction, etc.). The diabetes predicted by the score and other evaluation steps include, for example, type II Diabetes Mellitus and other diabetic conditions and pre-diabetic conditions.

Treatment

In one embodiment, a method of the invention comprises treating an evaluated subject, such as a subject that has been identified as having an increased risk (e.g. at risk or high risk) for developing diabetes.

Treatments useful in the present invention can include, for example, exercise regimens, dietary modification, metabolic surgery, administration of pharmaceuticals, and any treatment known for diabetes. Examples of dietary modification include a reduction of daily carbohydrate intake, very low carbohydrate diet ('VLCD', carbohydrate intake <20 g/day)) and calorie restriction. Examples of metabolic surgery include bariatric surgery, gastric bypass, biliopancreatic diversion, duodenal switch, and Roux-en-Y gastric bypass.

Optionally the treatment comprises administering an anti-diabetic agent. Optionally, the anti-diabetic agent is selected from an insulin sensitizer (e.g. a biguanidine), a peroxisome proliferator-activated receptor ('PPAR') activator (e.g. a thiazolidinedione), a bile acid, a bile acid sequesterant (e.g. colesevelam), a DPP-4 inhibitor, a GLP-1, a GLP-1 receptor agonist, a TGR5 agonist, a sulfonylurea (e.g. glibenclamide), a meglitinide, a Sodium-glucose co-transporter 2 ('SGLT2') inhibitor, an alpha-glucosidase inhibitor, a dopamine agonist (e.g. cycloset), an amylin mimetic (e.g. pramlintide), and an insulin or an analog or derivative thereof.

Optionally, the treatment comprises an anti-diabetic pharmaceutical, such as a small molecule. Examples include a biguanidine such as metformin or a thiazolidinedione such as rosiglitazone or pioglitazone.

Optionally, the treatment comprises administering a bile acid such as any of GHDCA, THDCA, HDCA, HCA, GHCA, THCA, or a derivative thereof. Such treatment agents are optionally administered orally or intravenously. Optionally, a treatment administered orally is formulated as a tablet, a capsule, a granule, or a dietary supplement. Other useful bile acids and bile acid derivatives are disclosed in U.S. Pat. No. 6,060,465 to Miljkovic et al, EP 0417725 A2 to Kramer et al, and U.S. Pat. No. 8,445,472 to Pellicciari. Other useful bile acids are those of Formula I and I taught herein. Other useful bile acids are any steroid carboxylic acids derived from cholesterol which bind or modulate (e.g. are an agonist of) G protein-coupled bile acid receptor 1 ('TGR5') or induce the production of Glucagon-like peptide-1 ('GLP-1'), including salts or conjugates thereof. For example, naturally occurring bile acids are often conjugated with glycine or taurine.

Optionally, the treatment comprises administering a compound of Formula I. Optionally R1 is selected from α-OH and β-O(CH2)nOH where n=1-10. Optionally, R2 is selected from α-OH, α-(CH2)nCH3 where n=0-6, or —O(CH2)nCH3 where n=0-6. Optionally, R3 is selected from α-OH and H. Optionally, R4 is selected from H and (CH2)nCH3 where n=0-6. Optionally, R5 is selected from —OH, NH(CH2)COOH, NH(CH2)2SO3H, O(CH2)nCH3 where n=0-1, or NH(CH2)nCO2Et where n=1-10. Optionally, R1-R5 are selected such that the compound is not a bile acid naturally occurring in a human. For example, HDCA, GHDCA, and THDCA all share the same R1=α-OH, R2=α-OH, R3=H, R4=H, wherein R5 is OH in HDCA, R5 is NH(CH2)COOH in GHDCA, and R5 is NH(CH2)2SO3H in THDCA. Alternatively R1-R5 can be any substituents.

Formula I

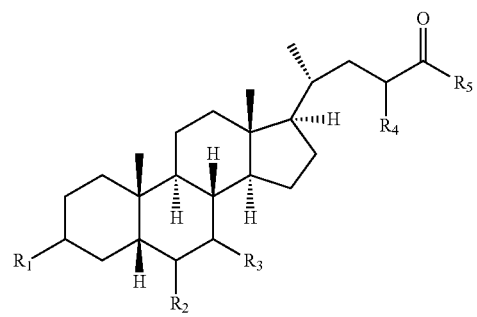

Optionally, the treatment comprises administering a compound of Formula II. Optionally R1-R5 and R7-R9 R1, R2, R3, R4, and R5 are independently hydrogen or XL where X is nothing, O, S, NH or NL and L is hydrogen, metallic ion, halogen, an alkyl or alkenyl radical having up to 10 carbon atoms, which is branched or unbranched, a cycloalkyl radical having 3 to 8 carbon atoms, or a benzyl radical which is unsubstituted or substituted 1 to 3 times by F, Cl, Br, $(C_1-C_4)$-alkyl or $(C_1-C_4)$-alkoxy; R6 is (CH2)n where 0≤n≤5, and where L is bonded to R1, L can alternatively be an amino acid. Optionally R1 is selected from α-OH and β-O(CH2)nOH where n=1-10. Optionally, R2 is selected from α-OH, α-(CH2)nCH3 where n=0-6, or —O(CH2)nCH3 where n=0-6. Optionally, R3 is selected from α-OH and H. Optionally, R4 is selected from H and (CH2)nCH3 where n=0-6. Optionally, R5 is selected from OH, NH(CH2)COOH, NH(CH2)2SO3H, O(CH2)nCH3 where n=0-1, or NH(CH2)nCO2Et where n=1-10. Optionally, R6 is selected from (CH2)n where n=1-5. Optionally, R7 is selected from H, $C_1-C_3$ alkyl, and OR10. Optionally, R8 is selected from H, $C_1-C_3$ alkyl, and OR11. Optionally, R9 is selected from H, $C1-C_3$ alkyl, and OR12. Optionally, R10-R12 are each selected from H and $C1-C_3$ alkyl. Alternatively R1-R12 can be any substituents.

Formula II

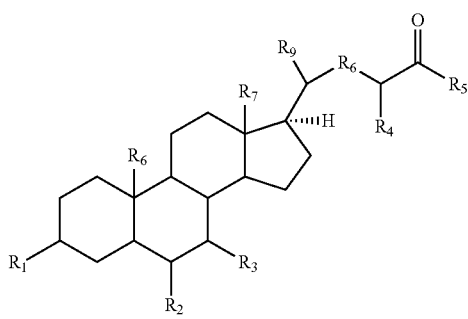

The invention also contemplates a salt, solvate, hydrate, or prodrug of a compound of Formula I or II or a treatment comprising such.

The invention also contemplates compounds and treatments comprising a compound of Formula I or II conjugated to another compound (e.g. amino acid such as glycine or taurine), for example, wherein the conjugate is formed at R5, where R5 comprises O, N, or S, or wherein the conjugate is formed at an O, N, or S replacing a ring hydrogen of Formula I or II. Optionally, a compound of Formula I or II is selected that increase the production of GLP1, e.g. in a TGR5 independent manner. Any example of an assay for such is detailed in Example 20.

Optionally, the treatment comprises administering a combination of agents, for example, a bile acid (e.g. HDCA and/or HCA) or analog thereof, and another anti-diabetic agent taught herein (e.g. metformin or a thiazolidinedione).

Optionally, the treatment comprises administering a dipeptidyl peptidase-4 ('DPP-4') inhibitor. Optionally the DPP-4 inhibitor is selected from sitagliptin, vildagliptin, saxagliptin, linagliptin, gemigliptin, anagliptin, teneligliptin, alogliptin, trelagliptin, dutogliptin, omarigliptin (mk-3102), berberine, and lupeol.

Optionally, the treatment comprises administering a glucagon-like peptide-1 ('GLP-1') receptor agonist. Optionally the GLP-1 receptor agonist is selected from exenatide, liraglutide, lixisenatide, albiglutide, and dulaglutide.

Optionally, the treatment comprises administering a GLP-1. Examples of useful GLP-1 peptides include native GLP-1 (e.g. human) or GLP-1 mimetics such as those taught by Gupta (Gupta V. Glucagon-like peptide-1 analogues: An overview. Indian Journal of Endocrinology and Metabolism. 2013; 17(3):413-421. doi:10.4103/2230-8210.111625), U.S. Pat. No. 5,545,618 to Buckley et al, and U.S. Pat. No. 6,458,924 to Knudsen et al.

Optionally, the treatment comprises administering a TGR5 agonist. Examples of useful TGR5 agonists include 1,4-diazepan-2-one compounds and compounds taught in WO 2016/149628A1 to Kasatkin et al, Russian patent RU2543485C2 (Grant date 10 Mar. 2015), and US 2013/0085157 A1 to Smith et al. Other useful TGR5 agonists include 2-thio-imidazole derivatives such as the compound 6g (Discovery of a Potent and Orally Efficacious TGR5 Receptor Agonist. Agarwal et al. Desai ACS Medicinal Chemistry Letters 2016 7 (1), 51-5), and RDX98940.

Optionally, the treatment comprises administering a SGLT2. Optionally, the SGLT2 is selected from empagliflozin, canagliflozin, dapagliflozin, and ipragliflozin.

Optionally, the treatment comprises administering an alpha-glucosidase inhibitor. Optionally, the alpha-glucosidase inhibitor is selected from Acarbose, Miglitol, and Voglibose.

Optionally, the treatment comprises administering a bile acid sequesterant, for example, cholestyramine, colesevelam, or colestipol.

Other useful treatments include administering any agent taught in WO 2016094729A1 (Boehm et al.), US 20130196898 A1 (Dugi et al.), or U.S. Pat. No. 8,513,264 B2 (Mark et al.).

Optionally, the treatment is any standard of care for a diabetic individual, e.g. a diabetic individual with type 2 diabetes.

Without being bound by theory, the present inventor believes that the treatments taught herein can be prescribed or administered in a therapeutically effective amount that will delay, reduce, or prevent the onset of diabetes, and optionally modify the biomarker levels in the subject to lower the diabetes risk of the subject according to a measured biomarker level or calculated score based on measured biomarker levels. For example, the inventor conducted a study, from which it was discovered that a VLCD reduces the P/S ratio and serum triglycerides in subjects that are at risk for developing diabetes. Biomarkers that can be measured to demonstrate a therapeutic effect include biomarkers of the present invention or a panel thereof, or any known biomarker of diabetes status such as of fasting blood glucose, insulin, HBA1c, GLP1, or TGR5.

While the present invention contemplates the treatment of subject in which biomarkers of the present invention have been measured, the invention also contemplates the use of any of the treatments disclosed herein, even outside of the diagnostic methods of the invention. For example, a method of treatment disclosed herein can be used following a diagnostic method of the invention or without performing a diagnostic method of the invention. For example, the inventor believes that certain therapeutic methods disclosed herein such as the administration of HDCA and/or HCA or analog or derivative thereof are not known in the prior art and provide novel methods of treating a subject having diabetes, pre-diabetes, a pre-diabetic condition or a subject at-risk for developing any of such. Further, the invention contemplates a compound per se of any compounds of Formula I or II (e.g. irrespective of a method of using the compound).

Monitoring

In one embodiment, a method of the invention comprises monitoring the level of one or more biomarkers. A method of monitoring according to the present invention comprises providing a first biological sample and a second sample, wherein the first sample is obtained from the subject at a first time and the second biological sample is obtained from the subject at a second time, wherein the second time is later than the first time, measuring the level of the one or more biomarkers in each of the first sample and second sample, and either comparing the measured levels from the first sample to the measured levels of the second sample, or correlating the levels measured in each sample with diabetes risk and comparing the diabetes risk correlated from the first sample to the diabetes risk correlated from the second sample.

Optionally, the first time is prior to the subject receiving a treatment and the second time is following the subject receiving the treatment. Accordingly, measuring the levels of biomarkers according to the present invention optionally further allows for the diabetes risk of a subject to be monitored or a course of treatment to be monitored.

Optionally, the treatment is modified if the comparison of the levels of the one or more biomarkers from the first sample and second sample do not indicate a predetermined (e.g. substantial) reduction in diabetes risk or do not indicate a predetermined (e.g. substantial) change in the level of the one or more biomarker levels.

Accordingly, identifying a subject having increased risk for developing diabetes can be used, e.g. to enable the selection and initiation of various treatment regimens (or therapeutic interventions) in order to delay, reduce or prevent the onset of type 2 diabetes in the subject. Measuring the levels of biomarkers optionally further allows for the course of treatment to be monitored. In this method, a first biological sample can be provided from the subject prior to undergoing treatment and a second biological sample can be provided from the subject following the treatment.

Kits

In one embodiment, a method of the invention provides a kit for detecting one or more biomarkers of a panel of the invention. Included in the kit are one or more internal standards for detecting one or more biomarkers of a panel of the invention. Collectively, the one or more internal standards provide at least one internal standard for each biomarker of the panel.

Figure 9A:
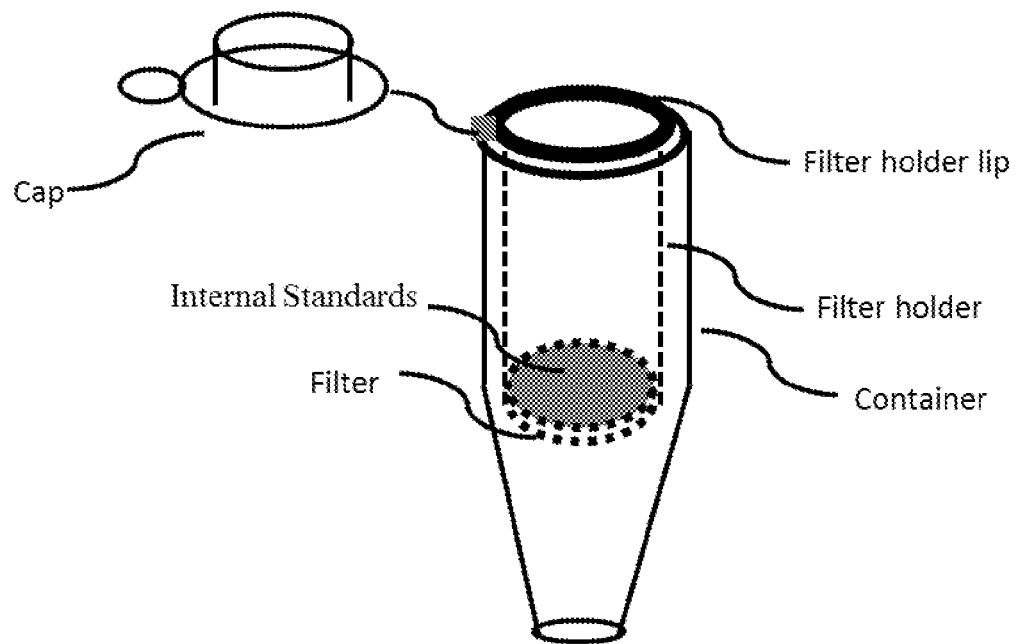
FIG. 9A and FIG. 9B depict a kit of the invention.
Figure 9B:
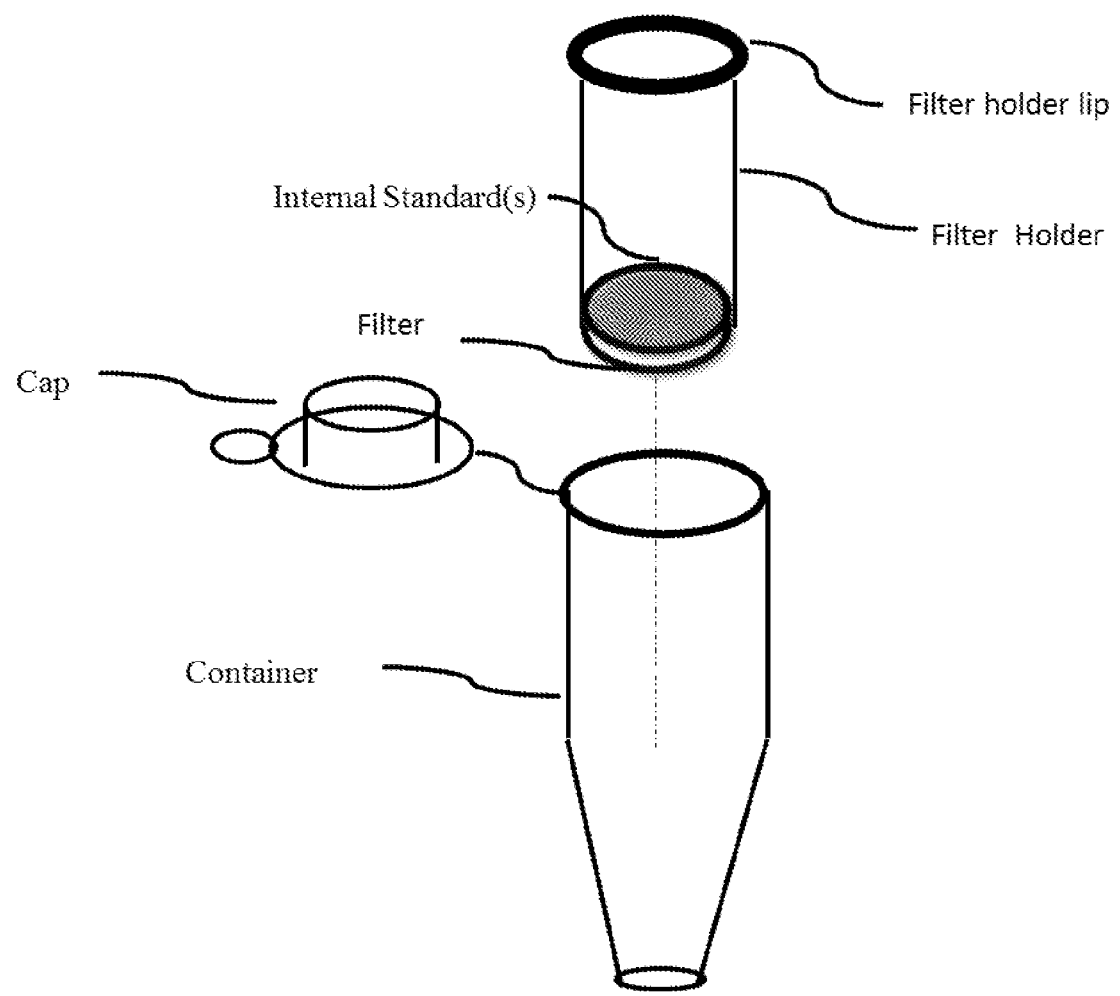
Figure 10:
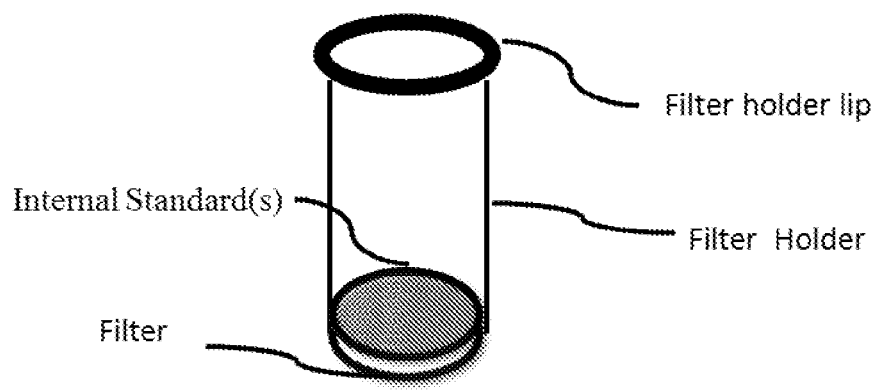
FIG. 10 depicts a kit of the invention.

Optionally, the kit comprises a container, a filter, or both (e.g. a filter in a container). Optionally the container comprises the one or more internal standards. Additionally or alternatively, a filter comprises the one or more internal standards. Examples of such kits are depicted in FIGS. 9A, 9B, and 10.

Optionally, the internal standards configured for GC-MS or LC-MS.

Optionally, the one or more internal standards are a plurality of internal standards. Optionally, the internal standards are provided in a mixture. Alternatively, one or more of the plurality of internal standards can be separated from each other.

Optionally, optionally, the one or more internal standards are provided in solid or liquid form. Optionally, the one or more internal standards dehydrated or freeze-dried (e.g. by lyophilization). Solid internal standards can be, for example, suspended into solution prior to use of the kit.

Optionally, the internal standards are any taught herein.

Optionally, the one or more internal standards comprise a labeled steroid acid (e.g. bile acid), a labeled fatty acid, and/or a labeled amino acid. The label can be, e.g. an isotope such as $(2)H$ or $(13)C$.

Optionally, each internal standard is the same compound as a corresponding biomarker of the panel, except it has one or more of its atoms replaced with a stable isotope of the one or more atoms (e.g. $(2)H$, $(13)C$, $(15)N$, or $(18)O$). For example, a set of internal standards for a given panel of biomarkers can be provided by providing an isotope labeled variant of each biomarker. Optionally, the panel is any panel selected from the panels A-BZ listed in FIGS. 12A-12C.

Optionally, the kit comprises a filter. Optionally, the one or more internal standards are deposited on the filter (e.g. as depicted in FIG. 9 and FIG. 10). Optionally, the filter is provided in a container or is configured for placement in or on the container (e.g. as depicted in FIG. 9 and FIG. 10). Optionally, the filter is removable from the container (e.g. as depicted in FIG. 9A). Optionally, the filter is mounted to a filter holder, e.g. a filter holder that can be placed in a container (e.g. a cylindrical filter holder and/or a filter holder having a lip as depicted in FIG. 9 and FIG. 10), for example a filter holder that is itself a container (with solid side walls) that can be placed inside another container, e.g. as depicted in FIG. 9A. Optionally, when the filter is in the container, the container can hold a volume of liquid on each side of the filter, e.g. by providing a void or cavity on each side of the filter (e.g. as depicted in FIG. 9B). Such a kit optionally allows the container to be centrifuged to force a solution from a first side of the filter through the filter to a second side of the filter.

The filter can be configured such that the filtrate includes the internal standards and biomarkers supplemented to the first side of the filter. The filtrate can then be analyzed (e.g. via GCMS or LCMS) to measure the biomarkers and internal standards, e.g. by removing the filter. Optionally, the filter is any filter with a pore size that allows the passage of biomarkers of the panel and internal standards to pass through but retains other components such as proteins (e.g. precipitated proteins). For example, the filter can be a 0.22 µm filter. Optionally, the filter is a Polyvinylidene Fluoride, cellulose (e.g. Cellulose acetate), or nylon filter. Optionally, the filter comprises an antioxidant such as butylated hydroxytoluene (BHT).

Optionally, the one more internal standards are mixed with an antioxidant such butylated hydroxytoluene (BHT). Such an anti-oxidant can be provided, e.g. to product internal standards such as fatty acids from degradation, thus extending the shelf life of the kit.

Optionally, the kit comprises at least container comprising the one or more internal standards therein. Optionally, the container is a tube, vial or multi-welled or multi-chambered plate. The kit may have a single container (e.g. well or chamber), or may have multiple containers (e.g. wells or chambers). For example, the kit can comprise a multi-welled plate (e.g., a microtiter plate such as a 96-well microtiter plate). Other analogous containers are also contemplated. In some kits, the container may be appropriate for use in measurement of the internal standards and quantitation of the one or more metabolites to be assessed in a subject sample. In some kits, the container used for measurement of internal standards and quantitation of one or more metabolites in a subject sample is configured to be used for spectral analysis such as, for example, chromatography-mass spectrometry. For example, the container may be configured for GC-TOFMS and/or LC-TQMS. In other kits, the container may be configured for other analytical tests specific for one or more of the metabolites to be assessed in a subject sample (e.g., enzymatic, chemical, colorimetric, fluorometric, etc.).

Some kits include a plurality of containers. For example, some kits include one or more containers having the internal standards. In addition, some kits include one or more containers having the internal standards and an additional container to be used in measurement of the internal standards and quantitation of the one or more metabolites to be assessed in a subject sample (e.g., a multi-welled plate or another tube or vial). In some kits, there is a single container that is used to contain the one or more internal standards and used in measurement of the internal standards and quantitation of the one or more metabolites to be assessed in a subject sample.

In kits comprising a multi-welled, multi-chambered, or other multi-container device, the internal standards may optionally be located in one or more wells or chambers upon distribution of the kit for use. In some kits, the internal standards are provided outside of the container and must be dispersed into the container(s) while using the kits.

The container of the kit can also be configured to accept a biological sample from at least one subject. For example, where the kit includes multiple chambers or wells, a biological sample from a subject may be distributed into one or more chambers or wells. In some instances, one or more amounts of a subject sample may be distributed into a plurality of chambers or wells. The container of the kit is generally configured to accept fluid samples (e.g., fluid biological samples or solid biological samples that have been processed to obtain a fluid for analysis).

Some kits also include reagents useful for measurement of the internal standards and quantitation of the one or more metabolites to be assessed in a subject sample. These reagents may be included in the kit in one or more additional containers.

An examplary kit may comprise an internal standard each provided in the same or a separate container. The container is optionally provided in the form of a microtiter plate, e.g. configured for use with either a GC-MS or LC-MS device. The microtiter plate will have a sufficient number of wells to receive at least one internal standard. The internal standards have known concentrations and will be already in the container or used to dispense a known amount of each internal standard into separate wells of the microtiter plate. After dispensing the internal standards into the analytical container, a portion of the subject sample can also be dispensed into the microtiter plate. Either a single portion of a subject sample is dispensed or a plurality of portions can be dispensed. If a plurality of portions is dispensed into the microtiter plate, each portion may be dispensed into a separate well. In addition, if a plurality of portions is dispensed into the microtiter plate, each portion may be of a different amount.

Computers and Modules and Automated Systems

Methods of the invention can be implemented through the use of a computer configured to perform one or more steps of measuring, correlating, and reporting. Accordingly, one embodiment of the present invention provides a non-volatile memory comprising a module configured for measurement (e.g. converting measurement signals from an analytical machine into biomarker levels), evaluating (e.g. correlating the biomarker levels with diabetes risk or inputting the biomarker levels into a mathematical model that computes a score), and/or reporting the result of the evaluation. Optionally, the invention provides a computer comprising a microprocessor and the non-volatile memory, wherein the microprocessor is configured to carry out the module.

The steps of measurement and/or evaluating (e.g. correlating, comparing values or a calculating score), can be performed using a computer comprising a module there for (e.g. program stored on non-volatile memory and carried out by a microprocessor). For example, a measurement module can be provided that interprets a signal indicative of biomarker level from a connected measuring device (e.g. 'MS') and calculates the level of the of the biomarker there from. Optionally, the measurement module is configured to normalize the level of the biomarker by comparing the signal to a signal obtained (e.g. via MS) from a respective internal standard. As another example, an evaluation module can be provided that makes a determination of diabetes risk using the biomarker level as an input into an algorithm (e.g. an algorithm that computes risk score or likelihood of developing diabetes or that compares biomarker levels to comparator levels).

Optionally, the module is configured to report the results of the evaluation. Examples of reporting mechanisms include visible display, a link to a data structure or database, or a printer. The reporting means can optionally be a data link to send test results to an external device, such as a data structure, data base, visual display, or printer.

Methods of the present invention can be automated using diagnostic test systems that utilize a computer or an analog machine. Tests to measure biomarkers and biomarker panels can be implemented on a wide variety of diagnostic test systems. Diagnostic test systems can be apparatuses that typically include means for obtaining test results from biological samples. Examples of such means include modules that automate the testing (e.g., detection assays). Diagnostic test systems can optionally be configured to handle multiple biological samples and can be programmed to run the same or different tests on each sample. Diagnostic test systems optionally include means for collecting, storing and/or tracking test results for each sample, usually in a data structure or database. Examples include physical and non-volatile storage devices (e.g., hard drives, flash memory, magnetic tape, or paper print-outs). Optionally, diagnostic test systems a means for reporting test results. Examples of reporting means include visible display, a link to a data structure or database, or a printer. The reporting means can optionally be a data link to send test results to an external device, such as a data structure, data base, visual display, or printer.

Biomarkers

According to the present invention, a panel comprising one or more biomarkers is selected and used for a method or kit of the invention.

Optionally, the panel comprises one or more biomarkers of FIG. 11.

Optionally, the panel is selected from panels A-BZ listed in FIG. 12A-12C. The biomarkers present in each panel or indicated by an "x". For example, Panel A includes GHDCA (or % GHDCA) and the ratio of C16:0/C18:0 fatty acids. Other useful panels can be produced by adding an additional biomarker (e.g. any listed in FIG. 11) to any of panels A-BZ.

A biomarker selected for level measurement of level can optionally be an analyte (e.g. palmitic acid ('P') or stearic acid (S')) such as the absolute level of the analyte or it can be a calculation based on a plurality of analyte levels. For example, the calculation can be a ratio of analytes (e.g. ratio of P/S) or a relative level (e.g. percent) of one or more analytes compared to one or more analytes (e.g. % GHDCA of total bile acids) or the sum of analyte levels (e.g. total triglycerides). When a first biomarker is calculated as a ratio of a second biomarker to a third biomarker, the first biomarker level can be measured or determined by measuring the level of the second biomarker and the third biomarker and calculating the ratio from the measured levels of the second biomarker and the third biomarker. Optionally a panel biomarker is provided by the sum of the amount or quantity of at least two biomarker taught herein (e.g. GHDCA+GHCA or % GHDCA+% GHCA or sum of all BCAAs).

Optionally, a panel of biomarkers according to the present invention comprises 1, 2, 3, 4, 5, 6, 7, 8, 9, or 10 biomarkers, or more.

In any aspect of the invention, the panel optionally comprises one or more bile acids, one or more amino acids, one or more free fatty acids, and/or one or more one or more blood biochemical indices.

Optionally, the one or more bile acid biomarkers are selected from Glycohyodeoxycholic acid ('GHDCA'), percent GHDCA (% GHDCA), Taurohyodeoxycholic acid ('THDCA'), percent THDCA ('% THDCA'), Hyodeoxycholic acid ('HDCA'), percent HDCA ('% HDCA'), Taurochenodeoxycholic acid ('TCDCA'), Taurodeoxycholic acid ('TDCA'), Glycohyocholic acid ('GHCA'), percent GHCA (% GHCA), Hyocholic acid ('HCA'), percent HCA ('% HCA'), Taurohyocholic acid ('THCA'), and percent THCA ('% THCA'), and Taurolithocholic acid ('TLCA'). A low or level decreased level (e.g. relative to a subject that did not later develop diabetes, or relative to a control or comparator) of any of these bile acids can contribute to an increased risk of developing diabetes. According to the present invention, the percent of a bile acid (e.g. % GHDCA) is determined with respect to all bile acids present in the sample, for example percent by mass or percent by number of molecules. Optionally, when a panel comprises a plurality of bile acids, each of the bile acids is measured as percent bile acid or each of the bile acids is measured as the absolute level of bile acid.

Optionally, the one or more one or more amino acids comprise one or more branch chain amino acids ('BCAAs') and/or one or more aromatic amino acids ('AAAs'). Optionally, the BCAAs comprises one or more of leucine, isoleucine, and valine. Optionally, the AAAs comprises phenylalanine and/or tyrosine.

Optionally, the one or more one or more amino acids comprise one or more of Alanine, Aspartic acid, Beta-Alanine, Creatine, Cystine, Glycine, Histidine, Isoleucine, Leucine, Methionine, N-Acetyl-L-aspartic acid, Proline, Pyroglutamic acid, Serine, S-Methyl-cysteine, Threonine, Tryptophan, Tyrosine, Valine, and Phenylalnine.

Optionally, the one or more one or more free fatty acids comprises one or more of Lauric acid (C12:0), Myristic acid (C14:0), 12-Methyltridecanoic acid (C14:0 iso), Myristoleic acid (C14:1 n5), 13-Methylmyristic acid (C15:0 iso), Pentadecanoic acid (C15:0), Palmitic acid (C16:0), 14-methylpentadecanoic acid (C16:0 iso), Palmitoleic acid (C16:1 n7), Palmitelaidic acid (C16:1 t9), 15-Methylpalmitic acid (C17:0 iso), Margaric acid (C17:0), Stearic acid (C18:0), 16-Methylmargaric acid (C18:0 iso), Oleic acid (C18:1 n9), Elaidic acid (C18:1 t9), Linoleic acid (C18:2 n6), α-Linolenic acid (C18:3 n3), Nonadecanoic acid (C19:0), Nonadecenoic acid (C19:1 n9), Eicosenoic acid (C20:1 n9), dihomo-γ-linolenic acid (C20:3 n6), Arachidonic acid (C20:4 n6), Erucic acid (C22:1 n9), Docosatetraenoic acid (C22:4 n-6), Docosapentaenoic acid (C22:5 n-6), Eicosenoic acid (C20:1 n-9), C16:0/C18:0 ratio, C18:1 n9/C18:0 ratio, and C20:3 n6/C20:4.

Optionally, the one or more blood biochemical comprise one or more of total Triglycerides (TG), Gemoglobin A1c (HBA1c), Glucose, Insulin, High density lipoprotein (HDL), and Low density lipoprotein (LDL).

Optionally, the panel comprises:
a. one or more (e.g. each) of GHDCA or % GHDCA, THDCA or % THDCA, HDCA or % HDCA, HCA or % HCA, GHCA or % GHCA, and THCA or % THCA;
b. one or more (e.g. each) of Palmitic acid (C16:0), Stearic acid (C18:0), Oleic acid (C18:1 n9), dihomo-γ-linolenic acid (C20:3 n6), and Arachidonic acid (C20:4 n6);
c. one or more (e.g. each) of Isoleucine, Leucine, Tyrosine, Valine, and Phenylalanine;
d. TG;
e. a combination of (a) and (b), (a) and (c), (a) and (d), (b) and (c), (b) and (d), or (c) and (d);
f. a combination (a), (b), and (c);
g. a combination (a), (b), and (d);
h. a combination (a), (c), and (d); or
i. a combination (b), (c), and (d).

Optionally, the panel comprises a panel selected from panels A-BZ and further comprises HBA1c.

Optionally, the panel comprises a panel selected from panels A-BZ and further comprises total BCAA's.

Optionally, the panel comprises a panel selected from panels A-BZ and further comprises Tyrosine, Valine, or both.

Optionally, the panel comprises a panel selected from panels A-BZ and further comprises TG.

Optionally, the panel comprises a panel selected from panels A-BZ and further comprises C16:0/C18:0 ratio.

Through insight of the inventor and/or through discoveries detailed in the examples taught herein, the biomarkers listed in FIG. 11 and panels A-BZ listed in FIG. 12A-12C have been determined to provide diagnostic ability for evaluating diabetes risk. One skilled in the art can use biomarkers and biomarker panels taught herein to obtain diabetes risk correlations based there on, for example, scoring models based on a training set of individuals who did and did not develop diabetes over a period of time. While some biomarkers taught herein have previously been correlated with diabetes or diabetes risk, the inventor believes that the addition of certain other biomarkers which have not been previously linked diabetes or diabetes risk add substantial diagnostic power to such previously known biomarkers, thereby providing panels of the invention with a high capacity to identify subjects at risk for developing diabetes.

EXAMPLES

Example 1 Study Design and Population

Studies took place at the Shanghai Jiao Tong University Affiliated Sixth People's Hospital. The study protocols were approved by the local ethics committees. Written, informed consent was obtained from all participants.

Sample Set 1: A total of 312 subjects were selected from the Shanghai Obesity Study (SHOS) and enrolled in a cross-sectional study. The SHOS was a prospective study designed to investigate the occurrence and development of diabetes and its related diseases. Beginning in 2009, the SHOS recruited 5000 participants from four communities in Shanghai, China, which included a baseline study as well as, 1.5-, 3-, and 5-yr follow-up studies. Of the 312 subjects in the cohort, 132 healthy subjects were normal weight (NW), 107 subjects were either overweight or obese (HO), and 73 subjects had been diagnosed with T2D complicated with hypertension, high cholesterol or hypertriglyceridemia (UO). The clinical characteristic of the populations is shown in Table 1.

Sample Set 2: 10-year longitudinal study: 62 subjects were selected from the Shanghai Diabetes Study (SHDS). The SHDS cohort was a multi-stage stratified epidemiological study designed to assess the prevalence of diabetes and associated metabolic disorders. It was initiated in 1998, when 5,994 individuals were enrolled from two urban communities, Huayang and Caoyang Districts in Shanghai, China, and 1,250 of them completed the follow-up examination in Huanyang District between 2010 and 2011. Among 1,250 eligible participants, we selected 62 subjects who were overweight/obese and metabolically healthy at baseline, of which, 50 became unhealthy overweight/obese with diabetes (UO) and 12 remained healthy overweight/obese (HO) after ten years. The clinical characteristic of the populations is shown in Table 2.

TABLE 1

Clinical characteristics of NW, HO and UO subjects in the cross-sectional study.

|  | NW | HO | UO | P1 | P2 | P3 |
|---|---|---|---|---|---|---|
| Male (Female) | 47(85) | 39(68) | 37(36) | | | |
| 2 h-glucose (mmol/L) | 5.55 ± 0.09 | 5.74 ± 0.1 | 14.88 ± 0.5 | 1.52E−01 | 3.76E−32 | 8.69E−30 |
| Fasting glucose (mmol/L) | 5 ± 0.04 | 5.14 ± 0.03 | 8.04 ± 0.3 | 1.55E−03 | 1.25E−28 | 2.56E−25 |
| 0.5 h-glucose (mmol/L) | 8.18 ± 0.14 | 8.55 ± 0.14 | 13.34 ± 0.41 | 3.42E−02 | 1.49E−24 | 5.71E−22 |
| TG (mmol/L) | 0.82 ± 0.02 | 0.99 ± 0.03 | 2.38 ± 0.17 | 4.99E−05 | 9.26E−26 | 1.31E−18 |
| TC (mmol/L) | 4.28 ± 0.05 | 4.26 ± 0.05 | 5.44 ± 0.11 | 6.82E−01 | 1.64E−16 | 1.93E−16 |
| Age (years) | 45.721 ± 0.852 | 46.269 ± 0.788 | 57.111 ± 0.846 | 7.72E−01 | 1.42E−14 | 9.01E−15 |
| SBP (mmHg) | 114.61 ± 0.95 | 116.01 ± 1.06 | 137.54 ± 2.57 | 3.48E−01 | 1.16E−16 | 4.48E−14 |
| HOMA-IR | 1.3 ± 0.05 | 2.09 ± 0.1 | 3.89 ± 0.24 | 5.32E−11 | 2.32E−25 | 6.30E−12 |
| HOMA-β | 80.4 ± 3.16 | 115.8 ± 6.48 | 61.64 ± 4.21 | 5.96E−07 | 2.60E−04 | 8.91E−12 |
| 0.5 h-insulin (μU/ml) | 50.17 ± 2.14 | 67.75 ± 3.51 | 38.76 ± 3.58 | 1.80E−05 | 3.62E−05 | 7.89E−11 |
| 2 h-insulin (μU/ml) | 27.83 ± 1.47 | 36.82 ± 2.32 | 69.67 ± 5.9 | 1.27E−03 | 1.34E−14 | 1.63E−08 |
| LDL (mmol/L) | 2.47 ± 0.04 | 2.69 ± 0.04 | 3.29 ± 0.1 | 5.51E−04 | 3.15E−12 | 1.26E−07 |
| DBP (mmHg) | 72.21 ± 0.67 | 74.6 ± 0.82 | 81.91 ± 1.63 | 5.97E−03 | 9.29E−09 | 3.74E−05 |
| Waist (cm) | 72.72 ± 0.4 | 87.9 ± 0.75 | 92.39 ± 0.82 | 2.86E−35 | 7.56E−32 | 1.01E−04 |
| Uric acid (μmol/ml) | 274.47 ± 5.17 | 297.16 ± 7.29 | 328.95 ± 7.78 | 3.03E−02 | 1.13E−08 | 1.05E−03 |
| HDL (mmol/L) | 1.63 ± 0.03 | 1.4 ± 0.03 | 1.27 ± 0.03 | 3.27E−08 | 4.53E−15 | 1.34E−03 |
| Fasting insulin (μU/ml) | 5.78 ± 0.23 | 9.07 ± 0.41 | 11.03 ± 0.6 | 5.70E−11 | 6.25E−16 | 8.67E−03 |
| ALT (U/L) | 15.21 ± 0.6 | 19.13 ± 0.81 | 22.92 ± 1.19 | 7.59E−05 | 3.62E−09 | 1.44E−02 |
| BMI (kg/m$^2$) | 20.51 ± 0.06 | 27.11 ± 0.18 | 27.68 ± 0.3 | 2.78E−40 | 2.28E−32 | 1.37E−01 |
| Creatinine | 65.45 ± 1.2 | 65.21 ± 1.37 | 64.05 ± 1.72 | 7.60E−01 | 4.35E−01 | 6.12E−01 |
| AST (U/L) | 19.7 ± 0.4 | 20.27 ± 0.5 | 20.7 ± 0.66 | 3.49E−01 | 2.02E−01 | 7.02E−01 |
| Urea | 4.87 ± 0.1 | 4.85 ± 0.11 | 4.81 ± 0.1 | 7.58E−01 | 7.77E−01 | 9.97E−01 |

Note:

Values in Table 1 represent means ± SEM. P1, P2, P3 values are calculated using Mann-Whitney U test to compare the FFA differences between NW and HO, NW and UO, HO and UO, respectively. The variables are ordered by P3 values.

Abbreviations used:

2 h INS, 2 h insulin;

2 h PG, 2 h postprandial glucose;

DBP, diastolic blood pressure;

FINS, fasting insulin;

FPG, fasting plasma glucose;

HbA1c, glycated hemoglobin A1c;

HDL-C, high density lipoprotein cholesterol;

LDL-C, low density lipoprotein cholesterol;

MH, metabolically healthy;

NW, normal weight;

OW/OB, overweight or obese;

P/S, palmitic/stearic acid;

SBP, systolic blood pressure;

T2D, type 2 diabetes;

TC, total cholesterol;

TG, triglycerides.

TABLE 2

The baseline clinical characteristics of participants in the longitudinal study with 10-year follow-up.

|  | HO | UO | FC | P1 |
|---|---|---|---|---|
| Male (Female) | 1(11) | 15(35) |  |  |
| Age (years) | 39.92 ± 3.66 | 43.94 ± 1.83 | 1.02 | 5.80E−01 |
| BMI (kg/m$^2$) | 26.88 ± 0.47 | 26.89 ± 0.37 | 0.99 | 4.87E−01 |
| SBP (mmHg) | 109.22 ± 3.78 | 115.57 ± 1.7 | 1.05 | 3.74E−01 |
| DBP (mmHg) | 72.31 ± 2.55 | 74.33 ± 0.77 | 1 | 7.87E−01 |
| Fasting glucose (mmol/L) | 4.87 ± 0.12 | 4.7 ± 0.06 | 0.96 | 2.30E−01 |
| 2 h-glucose (mmol/L) | 5.1 ± 0.19 | 5.26 ± 0.16 | 0.99 | 7.01E−01 |
| Fasting insulin (μU/ml) | 7.4 ± 0.85 | 7.1 ± 0.48 | 0.85 | 4.65E−01 |
| 2 h-insulin (μU/ml) | 43.6 ± 11.43 | 39.42 ± 3.51 | 0.91 | 9.50E−01 |
| HOMA-IR | 1.61 ± 0.19 | 1.48 ± 0.1 | 0.83 | 3.83E−01 |
| TG (mmol/l) | 0.94 ± 0.09 | 1.14 ± 0.04 | 1.28 | 4.99E−02 |
| TC (mmol/l) | 4.17 ± 0.13 | 4.08 ± 0.07 | 0.93 | 4.98E−01 |
| HDL (mmol/l) | 1.31 ± 0.06 | 1.34 ± 0.03 | 1.01 | 5.09E−01 |
| LDL (mmol/l) | 2.74 ± 0.13 | 2.67 ± 0.06 | 0.92 | 5.04E−01 |

Note:
Values in Table 2 represent means ± SEM. FC values are fold changes ratios of medians in UO over HO group. P1 values are calculated using Mann Whitney-U test, and highlighted in bold if p < 0.05. OR (95% CI) are odd ratios (95% confidence intervals) for metabolic syndrome from logistic regression models. These models are adjusted for age, sex, BMI, HOMA-IR, and fasting glucose. P2 values are calculated from logistic regression models.

Diagnosis Criteria

A cutoff point of BMI 28 kg/m$^2$ was used to define obesity (≥28 kg/m$^2$), a BMI of 24 kg/m2 was used to define overweight (≥24 kg/m$^2$) and normal weight was defined as (<24 kg/m$^2$) based on the recommendation of overweight and obesity for Chinese population. Zhou B. Biomed Environ Sci 2002; 15(3):245-52. Clinical characteristics and metabolic markers associated with diabetes were examined for all the participants in the two independent studies in Example 1, including fasting glucose, oral glucose tolerance test (2h-glucose or OGTT), insulin level, systolic and diastolic blood pressure (SBP and DBP), total cholesterol (TC) and triglycerides (TG), and high-density lipoprotein and low-density lipoprotein (HDL and LDL). "Metabolically healthy" was defined as having all of the following: FPG ≤6.1 mmol/L, OGTT ≤7.8 mmol/L and no previous history of diabetes; SBP/DBP <140/90 mmHg and no previous history of high blood pressure; fasting plasma TG <1.7 mmol/L and fasting plasma HDL≥0.9 mmol/L (men) or ≥1.0 mmol/L (women), and no previous history of high cholesterol (TC <5.18 mmol/L); no cardiovascular or endocrine disease history. Pang et al., PLoS One 2014; 9(5):e97928. Failure to meet all of the criteria was classified as "metabolically unhealthy".

Glucose tolerance was categorized according to the American diabetes association criteria: normal glucose tolerance (NGT), FPG <6.1 mmol/L and 2h PG <7.8 mmol/L; two categories of impaired glucose regulation (IGR): a) impaired glucose tolerance (IGT), FPG <7.0 mmol/L and 2h PG ≥7.8 and <11.1 mmol/L, and b) impaired fasting glycemia (IFG), FPG <7.0 and ≥6.1 mmol/L and 2h PG <7.8); and T2D (FPG ≥7.0 mmol/L or 2h PG ≥11.1 mmol/L, or antidiabetic treatment. Association American Diabetes. Diabetes Care 2004; 27:S15-35.

Anthropometric and Biochemical Measurements

Each participant had a physical examination including measurement of height, weight, waist circumference and blood pressure. Body mass index (BMI) was calculated as weight (kg) divided by squared height (m$^2$). Waist circumference was measured at the horizontal plane between the inferior costal margin and the iliac crest on the mid-axillary line. Blood pressure was the average of three measurements made with a sphygmomanometer at two minute intervals.

After a fasting venous blood sample was collected, each participant received a 75 g oral glucose tolerance test. Plasma glucose levels were measured by the glucose oxidase method. Serum insulin was assayed used a bio-antibody technique (Linco, St Louis, Mo., USA). Serum triglycerides and high density lipoprotein cholesterol were determined by standard commercial methods on a parallel, multichannel analyser (Hitachi 7600-020, Tokyo, Japan). An experienced technician who was blinded to the study measured glycated haemoglobin A1c (HbA1c) using high performance liquid chromatography (HLC-73G7, Tosoh, Japan). All of the measurements were carried out within two hours of blood collection. Insulin resistance and β cell function were evaluated using the following formulas: (1) HOMA IR (mIU·mmol/L2)=fasting insulin (mIU/L)×fasting glucose (mmol/L)/22.5; (2) HOMA-β (mIU/mmol/L)=20×fasting insulin (mIU/L)/(fasting glucose (mmol/L)−3.5).

Example 2 Targeted Metabolomics Analysis of Bile Acids (BAs)

Serum Sample Preparation.

An aliquot of 50 μl of serum was mixed with 150 μl of methanol (contains 0.10 μM of cholic acid (CA)-d4, ursodeoxycholic acid (UDCA)-d4, and lithocholic acid (LCA)-d4 used as the internal standard). The mixture was then vortexed for 2 min, allowed to stand for 10 min, and then centrifuged at 20000 g at 4° C. for 10 min. An aliquot of 160 μL supernatant was transferred to a clean tube and vacuum dried. The residue was redissolved with equal amount of acetonitrile (0.1% formic acid) and water (0.1% formic acid) to a final volume of 40 μL. After centrifugation, the supernatant was used for ultra-performance liquid chromatography-triple quadrupole mass spectrometry (UPLC-TQMS) analysis.

Method Validation.

Each aliquot of 41 standard stock solutions was mixed to obtain a mixed stock solution. Calibration solutions containing all 41 BA standards were prepared at a series of concentrations of 0.610, 1.221, 2.441, 4.883, 9.766, 19.531, 39.063, 78.125, 156.250, 312.5, 625.0, 1250.000, and 2500.00 ng/mL in naïve pooled serum depleted of BAs using activated charcoal. The calibration curve and the corresponding regression coefficients were obtained by internal standard adjustment. All BAs were found to be linear over the measured range.

Instrumentation.

Serum BAs were measured according to methods previously reported with minor modifications. Xie, et al. 2015, J Proteome Res 14 (2), 850-859. A Waters ACQUITY UPLC system equipped with a binary solvent delivery manager and a sample manager (Waters, Milford, Mass.) was used throughout the study. The mass spectrometer was a Waters XEVO TQ-S instrument with an ESI source (Waters, Milford, Mass.). The entire LC-MS system was controlled by MassLynx 4.1 software. All chromatographic separations were performed with an ACQUITY BEH C18 column (1.7 μm, 100 mm×2.1 mm internal dimensions) (Waters, Milford, Mass.).

LC-MS Analysis.

The mobile phase consisted of 0.1% formic acid in LC-MS grade water (mobile phase A) and 0.1% formic acid in LC-MS grade acetonitrile (mobile phase B) run at a flow rate of 0.3 mL/min. The flow rate was 0.45 mL/min with the following mobile phase gradient: 0-1 min (5% B), 1-5 min (5-25% B), 5-15.5 min (25-40% B), 15.5-17.5 min (40-95% B), 17.5-19 min (95% B), 19-19.5 min (95-5% B), 19.6-21 min (5% B). The column was maintained at 45° C. and the injection volume of all samples was 5 µL.

The mass spectrometer was operated in negative ion mode with a 1.2 kv capillary voltage. The source and desolvation gas temperature was 150 and 550° C., respectively. The data was collected with multiple reaction monitor (MRM) and the cone and collision energy for each BA used the optimized settings from QuanOptimize application manager (Waters Corp., Milford, Mass.).

Data Analysis.

UPLC-TQMS raw data obtained with negative mode were analyzed using TargetLynx applications manager version 4.1 (Waters Corp., Milford, Mass.) to obtain calibration equations and the quantitative concentration of each BA in the samples. A Student's t test was used to investigate differences between the groups in BAs measurements. The resultant p values for all metabolites were subsequently adjusted to account for multiple testing by false discovery rate (FDR) method. Pike, Methods in Ecology and Evolution 2011, 2 (3), 278-282. We regarded p values of <0.05 as significant.

Example 3 Targeted Metabolomics Analysis of Free Fatty Acids (FFAs)

FFA Extraction.

The concentrations of free fatty acids (FFAs) were determined using the previously reported method with some modification. Püttmann et al., Clin Chem 1993; 39(5):825-32. In brief, 10 µL of isotope labeled internal standards (5 µg/mL of nonadecanoic-d37 acid and tridecanoic-d25 acid) was added to each 40 µL of serum sample, followed by 500 µL of isopropyl/hexane/phosphoric acid (2M) (40/10/1 by vol). Samples were then vortexed for 2 min. After incubating at room temperature for 20 min, 400 µL of n-hexane and 300 µL of water were added, vortexed and centrifuged at 12,000 rpm for 10 min. Then 400 µL of the upper organic layer was transferred to a new tube and 400 µL of n-hexane was added to the lower layer for further extraction. After vortex and centrifuge, all of the upper organic phase was then combined with the first supernatant and dried under vacuum. The residue was reconstituted with 80 µL of methanol and subjected to ultra-performance liquid chromatography quadrupole-time-of-flight mass spectrometry (UPLC-TQMS) analysis.

LC-MS Conditions.

An ACQUITY-ultra-performance liquid chromatography system (Waters Corporation, Milford, USA) equipped with a binary solvent delivery system and an auto-sampler (Waters Corporation, Milford, USA) was employed for the separation on a 100 cm×2.1 mm BEH $C_{18}$ column with 1.7 µm particles at 40° C. (Waters Corporation, Milford, USA). The optimal mobile phase consisted of water (solvent A) and acetonitrile/isopropyl alcohol (80/20 by vol, solvent B) and the flow rate was set at 0.4 mL/min. The injection volume was of 5 µL. A gradient elution condition was applied as follows: 70% B over 0~2 min, 70%~75% B over 2~5 min, 75%~80% B over 5~10 min, 80%~90% B over 10~13 min, 90%~100% B over 13~16 min, maintained for 5 min, then returned to 70% B over 21~22.5 min and re-equilibrated for 1.5 min. The mass spectrometric data was collected using a tandem triple quadrupole (TQ) mass spectrometry (Manchester, UK). ESI was used as the ionization source and the analysis was carried out in the negative mode. The following parameters were used: capillary voltage, 2500 V; sampling cone, 55 V; extraction cone, 4V; desolvation temperature, 450° C.; source temperature, 120° C.; desolvation gas flow, 650 L/h; cone gas flow, 50 L/h; Lm resolution, 4.7; Hm resolution, 15; scan time, 0.35 s, and inter scan time 0.02 s. Leucine enkephalin was used as the lock mass (m/z 554.2615) at a concentration of 100 ng/mL and flow rate of 0.2 mL/min, with a lockspray frequency of 20 s Example 4 Targeted Metabolomics Analysis of Amino Acids (AAs)

The serum levels of the amino acids (AAs) in all the enrolled participants were analyzed by ultra-performance liquid chromatography triple quadruple mass spectrometry (UPLC-TQMS, Waters, Milford, Mass., USA). In brief, 10 µL of isotope labeled internal standards (5 µg/mL of valine-d8, leucine-5,5,5-d3, isoleucine-2-d1, tyrosine-3,3-d2, and phenylalanine-3,3-d2) were added to each of 40 µL aliquot of serum sample. After diluted with 80 µL of water, the sample was extracted with 500 µL of a mixture of methanol and acetonitrile (1:9, v/v). The extraction procedure was performed at −20° C. for 10 min after 2 min vortexing and 1 min ultrasonication. The sample was then centrifuged at 4° C. at 12000 rpm for 15 min. An aliquot of 20 µL supernatant was vacuum-dried at room temperature. After that, the residue was redissolved by 100 µL of a mixture of methanol and water (1:1, v/v) with 1 µg/mL of L-2-chlorophenylalanine followed by the same vortexing, ultrasonication and centrifugation steps ahead. A volume of 80 µL supernatant was transferred into the sampling vial for UPLC-TQMS analysis (Waters, Manchester, U.K). A 5 µL aliquot of sample was injected into an ultra-performance liquid chromatography system (Waters, U.K.) with a 4.6 mm×150 mm, 5 µm Elispse XDB-C18 column (Agilent, USA). The column was held at 40° C. The elution procedure for the column was 1% for the first 0.5 min, 1-20% B over 0.5-9 min, 20-75% B over 9-11 min, 75-99% B over 11-16 min, and the composition was held at 99% B for 0.5 min, where A=water with 0.1% formic acid and B=acetonitrile with 0.1% formic acid for positive mode (ESI+) and the flow rate was 0.4 mL/min. A Waters XEVO-Triple Quadrupole MS was used for the mass spectrometry detection. The temperature for the source and desolvation gas was set at 150 and 450° C. respectively. The gas flow for cone and desolvation was 50 and 800 L/h respectively. The capillary voltage was set to 3.0 kV. All the compounds were detected in multiple reaction monitor (MRM) mode.

Example 5 Serum Triglyceride Analysis

The total triglycerides were determined using a serum triglyceride determination kit with enzymatic methods.

Example 6 Quality Controls (QCs)

Reproducibility is critical for unbiased profiling of metabolomics. The entire process of the metabolomic analysis was subject to stringent QC to ensure the data are reproducible. Three types of QC samples, including test mixtures, internal standards, and pooled biological samples, were used in the metabolomic procedures. In addition to the QC samples, conditioning and solvent blank samples were also used for obtaining optimal instrument performance, and 5% of randomly selected samples were repeated for assessing reproducibility. Test mixtures comprise of a group of commercially available standards with a mass range across the system mass range. They were analyzed at the beginning and end of each batch run to ensure that the instruments perform within the laboratory specifications [retention time stability, peak resolution, peak signal intensity, and mass accuracy (LC-MS only)]. Internal standards (chlorophenyl-alanine for LC-MS; chlorophenylalanine and heptadecanoic acid for GC-MS) were added to the test samples in order to monitor analytical variations during the entire sample preparation and analytical processes. For biomarker discovery, the internal QC criteria/metrics are 1) coefficient of variation (CV) ≤15% within 100 injections, and 2) CV ≤20% within 300 injections. The CV is defined as the ratio of the standard deviation to the mean peak of signal intensity. Pooled QC samples which combine serum aliquots from all the study subjects (or representative subjects depending on the number of samples to be tested) are used for assessing the overall reproducibility and correcting inter-batch variations. The QC samples were prepared with the test samples and injected at regular intervals (after every 10 test samples for GC-MS and for LC-MS, respectively) throughout the analytical run.

Example 7 Statistical Analysis

The raw data produced by UPLC-MS such as UPLC-TQMS were initially processed using TargetLynx applications manager version 4.1 (Waters Corp., Milford, Mass.) to detect peak signals, obtain calibration equations, and calculate the concentration of each metabolite. Manual examination and correction were needed to ensure data quality. All statistical computing and graphics were carried out using R and SIMCA 13.0.1 software (Umetrics, Sweden).

Prior to the statistical analysis, we examined the distribution of each continuous variable (i.e., clinical characteristics, metabolic markers and metabolite markers) using the Shapiro-Wilk test, and found that 90% of the variables deviated from normality, thus non-parametric tests were used for this study. We used the Mann-Whitney U test to compare each metabolic marker or metabolite markers between two sample sets, such as HO and UO group in the cross-sectional study. Variables with p-values <0.05 were considered statistically significant. Multivariate logistic regression models were used to estimate the relative risk of developing diabetes at different metabolite marker levels, adjusting for age, sex, BMI and other confounding factors. Also, p values <0.05 were considered significant from logistic regression analysis. We further calculated the ROC curve areas of metabolite markers to evaluate their performance of discriminating HO and UO group in the cross-sectional study and the predictive power of estimating the risk of developing diabetes.

Example 8 Correlation of Biomarkers with the Future Development of Type 2 Diabetes (T2D)

As depicted in Table 3, Significantly increased free fatty acids (FFAs), amino acids (AAs) and triglycerides (TG) concentrations were observed in overweight/obese subjects with T2D (UO) in the cross-sectional study. GHDCA and % GHDCA were decreased in overweight/obese subjects with T2D.

TABLE 3

The identified metabolite biomarkers in the cross-sectional study

| | NW (n = 132) | HO (N = 107) | UO (n = 106) | P1 | P2 | P3 |
|---|---|---|---|---|---|---|
| TG | 0.78 (0.02) | 0.94 (0.03) | 1.97 (0.17) | 5.40E-05 | 2.20E-26 | 4.49E-19 |
| C16:0 | 61.35 (1.23) | 62.67 (1.19) | 86.2 (2) | 4.64E-01 | 7.37E-19 | 5.39E-18 |
| C18:0 | 59.99 (1.04) | 63.97 (1.09) | 72.21 (1.71) | 2.58E-02 | 5.82E-09 | 1.57E-05 |
| C18:1 n9 | 35.82 (1.67) | 33.47 (1.46) | 56.59 (2.36) | 1.27E-01 | 6.47E-11 | 8.10E-15 |
| C20:3 n6 | 0.88 (0.02) | 0.9 (0.02) | 1.45 (0.05) | 5.71E-01 | 1.31E-24 | 5.93E-22 |
| C20:4 n6 | 7.51 (0.18) | 7.59 (0.19) | 10.65 (0.49) | 5.44E-01 | 1.72E-10 | 4.28E-09 |
| Valine | 1.02 (0.03) | 1.17 (0.02) | 1.26 (0.04) | 7.91E-06 | 8.27E-08 | 3.06E-02 |
| Leucine | 0.01 (0) | 0.01 (0) | 0.02 (0) | 5.21E-04 | 1.12E-06 | 3.37E-02 |
| Isoleucine | 0.08 (0) | 0.1 (0) | 0.1 (0) | 8.44E-04 | 1.94E-06 | 3.72E-02 |
| Phenyl-alanine | 0.06 (0) | 0.07 (0) | 0.07 (0) | 8.79E-04 | 2.55E-06 | 3.69E-02 |
| Tyrosine | 0.02 (0) | 0.02 (0) | 0.02 (0) | 5.14E-02 | 4.77E-03 | 2.39E-02 |
| C16:0/C18:0 | 1.01 (0.01) | 0.99 (0.01) | 1.19 (0.02) | 1.44E-01 | 8.10E-13 | 4.12E-16 |
| C18:1 n9/C18:0 | 0.62 (0.03) | 0.53 (0.02) | 0.88 (0.03) | 1.97E-02 | 3.88E-05 | 1.23E-09 |
| C20:3 n6/C20:4 | 0.11 (0) | 0.12 (0) | 0.14 (0) | 6.39E-01 | 9.99E-06 | 1.70E-04 |
| GHDCA | 4.35 (0.86) | 4.86 (1.4) | 2.26 (0.78) | 1.81E-04 | 7.66E-02 | 5.76E-03 |
| GHDCA (percent %) | 0.68 (0.18) | 0.71 (0.16) | 0.41 (0.12) | 3.87E-04 | 4.04E-02 | 3.27E-02 |

Note:
Values in Table 3 represent means ± SEM. The concentration unit of FFAs and AAs are µg/ml. The concentration unit of BAs is ng/ml. P1, P2, P3 values are calculated using Mann-Whitney U test to compare the FFA differences between NW and HO, NW and UO, HO and UO, respectively.

Example 9 AAs Predict Future Diabetes

The 62 overweight subjects in Example 1 had normal metabolic markers at baseline and 50 of them developed diabetes (UO) while 12 remained healthy (HO) according to their re-evaluation after ten years. There were no differences between these two groups at baseline according to their metabolic markers. However, the baseline serum levels of five AAs, Valine, Leucine, Isoleucine, Phenylalanine, and Tyrosine were significantly increased in the UO group (Table 4). This result confirmed that the baseline concentrations of these AAs are predictive of the development of future diabetes in these subjects. The predictive power of the five AAs, Valine, Leucine, Isoleucine, Phenylalanine, and Tyrosine for diabetes incident among MH-OW/OB subjects was further evaluated using univariate and multivariate models. Logistic regression models adjusting for age, sex, BMI, HOMA-IR and fasting glucose were fitted.

Logistic regression analyses showed that baseline AAs levels was a positive predictor (adjusted odds ratio (OR) 2.53 [95% CI: 1.68-3.81], P=4.79E-03) of diabetes, independent of sex, age, BMI, HOMA-IR, HOMA-β, FPG and 2hPG (Table 4). The receiver operating characteristic (ROC) curves for the combination of the five AAs has an area under the curve (AUC) of 0.82 (95% CI: 0.65-0.91, P=2.84E-03) (FIG. 1). Notably, an AUC of 1.0 indicates perfect prediction and an AUC of 0.5 indicates prediction equivalent to random selection.

TABLE 4

The baseline FFAs, AAs, BAs and TG levels of participants in the
longitudinal study and their ability for determining the risk of developing diabetes.

| | HO (n = 12) | UO (n = 50) | P1 | AUC under ROC | Sensitivity | Specificity | Odds Ratio (OR) (95% CI) | P2 |
|---|---|---|---|---|---|---|---|---|
| TG | 0.88 (0.09) | 1.13 (0.04) | 4.99E-02 | 0.82 (0.50-0.97) | 0.8 | 0.583 | 3.03 (1.09-8.41) | 3.31E-02 |
| C16:0 | 58.92 (11.05) | 74.59 (4.69) | 2.81E-01 | 0.60 (0.39-0.81) | 0.68 | 0.667 | 1.38 (0.62-3.10) | 4.29E-01 |
| C18:0 | 54.99 (8.64) | 63.24 (2.28) | 7.15E-01 | 0.54 (0.32-0.75) | 0.64 | 0.583 | 0.75 (0.38-1.48) | 4.08E-01 |
| C18:1 n9 | 16.89 (3.73) | 27.14 (1.78) | 2.10E-02 | 0.72 (0.54-0.90) | 0.72 | 0.75 | 3.74 (1.08-9.71) | 3.60E-02 |
| C20:3 n6 | 1.36 (0.33) | 2.47 (0.27) | 1.06E-02 | 0.74 (0.57-0.91) | 0.6 | 0.833 | 4.33 (1.02-18.36) | 4.67E-02 |
| C20:4 n6 | 5.63 (0.91) | 7.25 (1.62) | 6.26E-02 | 0.68 (0.48-0.88) | 0.72 | 0.667 | 4.01 (0.23-70) | 3.41E-01 |
| Valine | 0.73 (0.05) | 0.94 (0.16) | 5.30E-03 | 0.76 (0.62-0.91) | 0.84 | 0.667 | 1.55 (1.00-2.38) | 4.84E-02 |
| Leucine | 0.01 (0) | 0.02 (0.01) | 5.01E-03 | 0.76 (0.63-0.90) | 0.9 | 0.583 | 5.39 (1.04-28.06) | 4.52E-02 |
| Isoleucine | 0.06 (0.01) | 0.09 (0.06) | 2.97E-02 | 0.70 (0.55-0.86) | 0.7 | 0.75 | 1.15 (0.98-1.36) | 8.65E-02 |
| Phenylalanine | 0.03 (0) | 0.04 (0.02) | 3.01E-03 | 0.78 (0.64-0.91) | 0.62 | 0.833 | 1.87 (0.97-3.61) | 6.34E-02 |
| Tyrosine | 0.01 (0) | 0.02 (0.01) | 1.11E-02 | 0.74 (0.60-0.88) | 0.6 | 0.833 | 4.10 (0.94-17.91) | 6.07E-02 |
| C16:0/C18:0 | 0.99 (0.06) | 1.2 (0.04) | 6.58E-03 | 0.76 (0.60-0.91) | 0.62 | 0.917 | 1.69 (1.09-2.63) | 1.94E-02 |
| C18:1 n9/C18:0 | 0.32 (0.04) | 0.41 (0.02) | 6.58E-03 | 0.76 (0.59-0.92) | 0.56 | 0.917 | 3.12 (1.34-7.30) | 8.51E-03 |
| C20:3 n6/C20:4 | 0.23 (0.02) | 0.32 (0.01) | 4.48E-03 | 0.77 (0.62-0.91) | 0.92 | 0.5 | 5.12 (1.43-18.37) | 1.22E-02 |
| GHDCA | 5.07 (0.01) | 3.02 (0) | 1.46E-03 | 0.80 (0.63-0.97) | 0.9 | 0.833 | 0.35 (0.16-0.77) | 8.93E-03 |
| GHDCA (percent % of total BAs) | 0.75 (0.13) | 0.45 (0.12) | 1.77E-03 | 0.79 (0.63-0.96) | 0.82 | 0.75 | 0.26 (0.09-0.76) | 1.32E-02 |
| Combination of C16:0, C18:0, C18:1 n9, C20:3 n6, C20:4 n6 | 0.28 (0.51) | 2.07 (0.25) | 4.33E-04 | 0.83 (0.66-1) | 0.94 | 0.75 | 8.78 (1.92-40.17) | 5.06E-03 |
| Combination of Valine, Leucine, Isoleucine, Phenylalanine, Tyrosine | 0.66 (0.22) | 1.76 (1.37) | 2.84E-03 | 0.82 (0.65-0.91) | 0.88 | 1 | 2.53 (1.63-3.81) | 4.79E-03 |
| Combination of C16:0/C18:0, C18:1 n9/C18:0, and C20:3 n6/C20:4 | 0.46 (0.39) | 2.4 (0.2) | 6.88E-04 | 0.82(0.67-0.97) | 0.74 | 0.833 | 7.47 (2.09-26.67) | 1.96E-03 |

TABLE 4-continued

The baseline FFAs, AAs, BAs and TG levels of participants in the
longitudinal study and their ability for determining the risk of developing diabetes.

| | HO (n = 12) | UO (n = 50) | P1 | AUC under ROC | Sensitivity | Specificity | Odds Ratio (OR) (95% CI) | P2 |
|---|---|---|---|---|---|---|---|---|
| Combination of TG, C16:0, C18:0, C18:1 n9, C20:3 n6, C20:4 n6, Valine, Leucine, Isoleucine, Phenylalanine, Tyrosine, and GHDCA | 5.3 (0.43) | 8.16 (2.62) | 3.18E−05 | 0.92 (0.84-1) | 0.92 | 0.833 | 10.94 (1.32-56.55) | 8.37E−03 |

Note:
Values in Table 4 represent means ± SEM. The concentration unit of FFAs and AAs are µg/ml. The concentration unit of BAs is ng/ml. P1 values are calculated using Mann Whitney-U test. OR (95% CI) are odd ratios (95% confidence intervals) for metabolic syndrome from logistic regression models. These models are adjusted for age, sex, BMI, HOMA-IR, and fasting glucose. P2 values are calculated from logistic regression models.

Example 10 FFAs Predict Future Diabetes

The 62 overweight subjects in Example 1 had normal metabolic markers at baseline and 50 of them developed diabetes (UO) while 12 remained healthy (HO) according to their re-evaluation after ten years. There were no differences between these two groups at baseline according to their metabolic markers. However, the baseline serum levels of five FFAs, Palmitic acid (C16:0), Stearic acid (C18:0), Oleic acid (C18:1 n9), dihomo-γ-linolenic acid (C20:3 n6), and Arachidonic acid (C20:4 n6) were significantly increased in the UO group (Table 4). This result further confirmed that the baseline concentrations of these FFAs are predictive of the development of future diabetes in these subjects. The predictive power of the five FFAs, Palmitic acid (C16:0), Stearic acid (C18:0), Oleic acid (C18:1 n9), dihomo-γ-linolenic acid (C20:3 n6), and Arachidonic acid (C20:4 n6) for diabetes incident among MH-OW/OB subjects was further evaluated using univariate and multivariate models. Logistic regression models adjusting for age, sex, BMI, HOMA-IR and fasting glucose were fitted.

Figure 2:
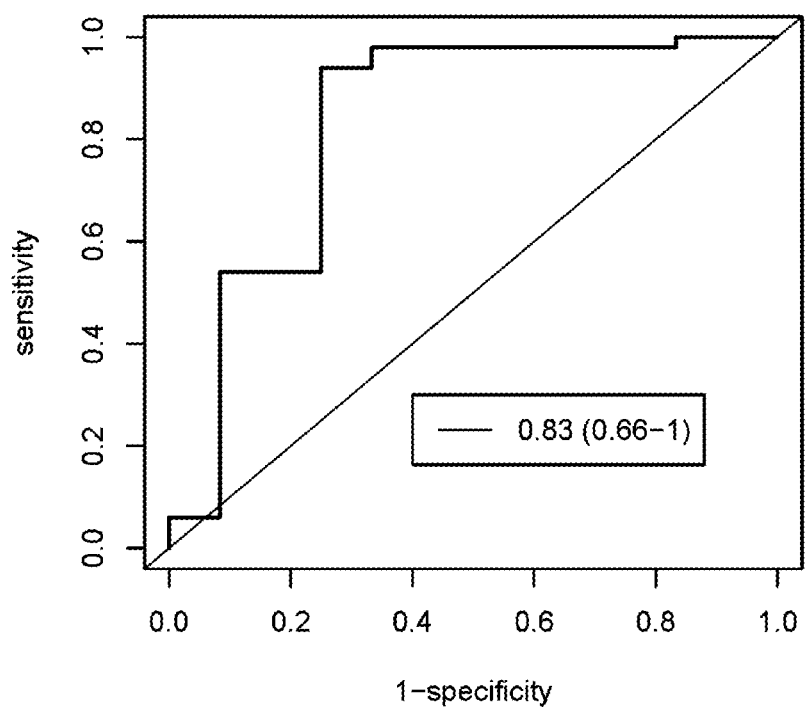
FIG. 2 depicts an ROC curve useful in carrying out a method of the invention.

Logistic regression analyses showed that baseline FFA levels was a positive predictor (adjusted OR: 8.78 [95% CI: 1.92-40.17], P=4.33E-04) of T2D, independent of sex, age, BMI, HOMA-IR, HOMA-β, FPG and 2hPG (Table 4). The receiver operating characteristic (ROC) curves for the combination of the five FFAs has an area under the curve (AUC) of 0.83 (95% CI: 0.66-1.00, P=5.06E-03) (FIG. 2). Notably, an AUC of 1.0 indicates perfect prediction and an AUC of 0.5 indicates prediction equivalent to random selection.

Example 11 Bile Acid Predicts Future Diabetes

The 62 overweight subjects in Example 1 had normal metabolic markers at baseline and 50 of them developed diabetes (UO) while 12 remained healthy (HO) according to their re-evaluation after ten years. There were no differences between these two groups at baseline according to their metabolic markers. However, the baseline serum levels of glycohyocholic acid (GHDCA) were significantly decreased in the UO group (Table 4). This result confirmed that the baseline concentration of GHDCA is predictive of the development of future diabetes in these subjects. The predictive power of GHDCA for diabetes incident among MH-OW/OB subjects was further evaluated using univariate and multivariate models. Logistic regression models adjusting for age, sex, BMI, HOMA-IR and fasting glucose were fitted.

Figure 3:
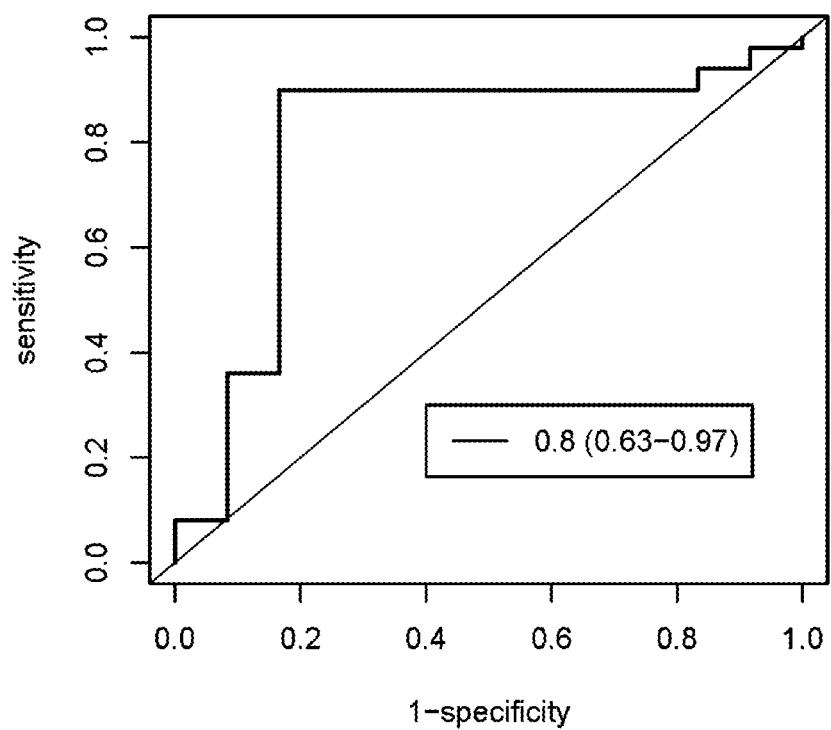
FIG. 3 depicts an ROC curve useful in carrying out a method of the invention.

Logistic regression analyses showed that baseline GHDCA level was a positive predictor (adjusted ORs 0.26 [95% CI: 0.09-0.76], P=8.93E-03) of diabetes, independent of sex, age, BMI, HOMA-IR, HOMA-β, FPG and 2hPG (Table 4). The receiver operating characteristic (ROC) curves for the GHDCA has an area under the curve (AUC) of 0.80 (95% CI: 0.63-0.97, P=1.46E-03) (FIG. 3). Notably, an AUC of 1.0 indicates perfect prediction and an AUC of 0.5 indicates prediction equivalent to random selection.

Example 12 TG Predicts Future Diabetes

The 62 overweight subjects in Example 1 had normal metabolic markers at baseline and 50 of them developed diabetes (UO) while 12 remained healthy (HO) according to their re-evaluation after ten years. There were no differences between these two groups at baseline according to their metabolic markers. However, the baseline serum levels of TG were significantly increased in the UO group (Table 4). This result confirmed that the baseline concentration of TG is predictive of the development of future diabetes in these subjects. The predictive power of TG for diabetes incident among MH-OW/OB subjects was further evaluated using univariate and multivariate models. Logistic regression models adjusting for age, sex, BMI, HOMA-IR and fasting glucose were fitted.

Figure 4:
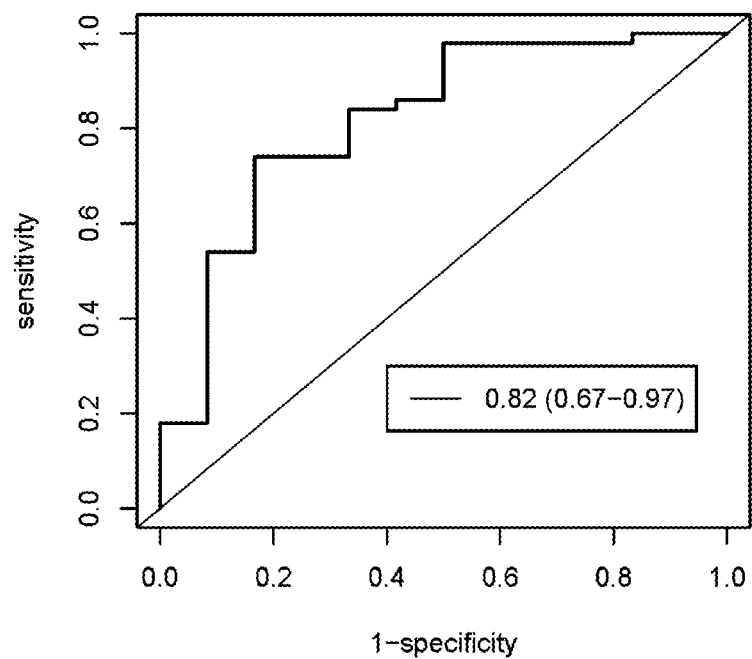
FIG. 4 depicts an ROC curve useful in carrying out a method of the invention.

Logistic regression analyses showed that baseline TG levels was a positive predictor (adjusted ORs 3.03 [95% CI: 1.09-8.41], P=3.31E-02) of T2D, independent of sex, age, BMI, HOMA-IR, HOMA-β, FPG and 2hPG (Table 4). The receiver operating characteristic (ROC) curves for the TG has an area under the curve (AUC) of 0.82 (95% CI: 0.50-0.97, P=4.99E-02) (FIG. 4). Notably, an AUC of 1.0 indicates perfect prediction and an AUC of 0.5 indicates prediction equivalent to random selection.

Figure 5:
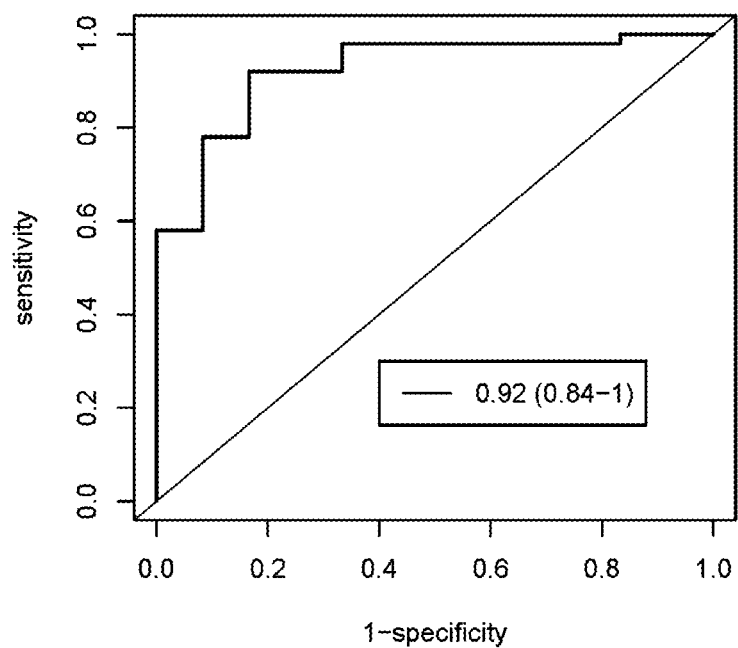
FIG. 5 depicts an ROC curve useful in carrying out a method of the invention

Example 13 The Combination of TG, C16:0, C18:0, C18:1 n9, C20:3 n6, C20:4 n6, Valine, Leucine, Isoleucine, Phenylalanine, Tyrosine, and GHDCA Predicts Future Diabetes in Metabolic Healthy OW/OB Individuals The predictive power of the combination of TG, C16:0, C18:0, C18:1 n9, C20:3 n6, C20:4 n6, Valine, Leucine, Isoleucine, Phenylalanine, Tyrosine, and GHDCA for diabetes incident among MH-OW/OB subjects was further evaluated using univariate and multivariate models. Logistic regression analyses showed that baseline levels of the combination of TG, C16:0, C18:0, C18:1 n9, C20:3 n6, C20:4 n6, Valine, Leucine, Isoleucine, Phenylalanine, Tyrosine, and GHDCA was a positive predictor (adjusted ORs 10.94 [95% CI: 1.32-56.55], P=8.37E-03) of diabetes, independent of sex, age, BMI, HOMA-IR, HOMA-$\beta$, FPG and 2hPG (Table 4). The receiver operating characteristic (ROC) curves for the combination of TG, C16:0, C18:0, C18:1 n9, C20:3 n6, C20:4 n6, Valine, Leucine, Isoleucine, Phenylalanine, Tyrosine, and GHDCA has an area under the curve (AUC) of 0.92 (95% CI: 0.84-1.00, P=3.18E-05) (FIG. 5). Notably, an AUC of 1.0 indicates perfect prediction and an AUC of 0.5 indicates prediction equivalent to random selection.

Example 14 Bioinformatics Tools to Inform the Individuals the Risk of Developing Diabetes Potential biomarkers were initially evaluated and selected using both univariate and multivariate analysis methods. The univariate methods include parametric statistics for normal-distributed variables (e.g., student t test and ANOVA), and non-parametric tests for those that failed to follow normal distribution (e.g., Mann Whitney U test and Kruskal Wallis test). Correlations between metabolites and their capabilities to estimate the risk of developing diabetes were further evaluated using Pearson or Spearman coefficients, clustering, partial least squares (PLS) methods, and logistic regression. With a list of potential biomarkers, a bioinformatics method was developed in this invention, which is based on logistical regression models, to obtain the optimal combination of biomarkers. A panel of biomarkers including Glycohyodeoxycholate (GHDCA), Palmitic acid (C16:0), Stearic acid (C18:0), Oleic acid (C18:1 n9), dihomo-$\gamma$-linolenic acid (C20:3 n6), Arachidonic acid (C20:4 n6), Valine, Leucine, Isoleucine, Phenylalanine, Tyrosine, and triglycerides (TG) in Table 3 are demonstrated to have powerful prediction ability for future diabetes.

A panel of biomarkers (Table 4) that included TG, 5 FFAs including Palmitic acid (C16:0), Stearic acid (C18:0), Oleic acid (C18:1 n9), dihomo-$\gamma$-linolenic acid (C20:3 n6), and Arachidonic acid (C20:4 n6), 5 AAs including Valine, Leucine, Isoleucine, Phenylalanine, and Tyrosine and GHDCA, achieved powerful predictive performance according to ROC curve analysis; the ROC curve area was 0.92 (95% CI: 0.84-1). According to the Yuden index calculated from the ROC model, the optimal threshold of the score for the combined biomarkers was 7.08, which can be used to predict the risk of developing diabetes. Individuals who have the score greater than 7.08 have high risk of developing diabetes in the future.

Example 15 Kits

An example Kit of the invention includes known amounts of isotope labeled (e.g. C13 labeled) internal standards corresponding the biomarker panel for non-diabetic individuals or diabetic patients to be monitored. The kit may include a single mixture of all the internal standards to be assessed, or may include a separate amount of each internal standard. The amounts of each internal standard in the metabolite profile to be assessed can be measured and used for comparison to the corresponding amount of a corresponding biomarker in a sample from a subject. Each internal standard may be in solid form or in liquid form in the distributed kits. If the internal standards are in solid form, they are to be suspended into solution prior to use of the kit. Kits optionally comprise at least one labeled variant of a metabolite biomarker selected from the metabolites listed in Table 3.

Example kits can include at least one container configured to contain the internal standards in the metabolite profile for non-diabetic individuals to be assessed. The container may be a tube, a vial or a multi-welled or multi-chambered plate. The container may have a single well or chamber, or the container may have multiple wells or chambers. For example, the container may be a multi-welled plate (e.g., a microtiter plate such as a 96-well microtiter plate). Other analogous containers are also appropriate. In some kits, the container may be appropriate for use in measurement of the internal standards and quantitation of the one or more biomarkers to be assessed in a subject sample. In some kits, the container used for measurement of internal standards and quantitation of one or more metabolites in a subject sample is configured to be used for spectral analysis such as, for example, chromatography-mass spectrometry. For example, the container may be configured for GC-TOFMS and/or LC-TQMS. In other kits, the container may be configured for other analytical tests specific for one or more of the metabolites to be assessed in a subject sample (e.g., enzymatic, chemical, colorimetric, fluorometric, etc.). The container may be configured to hold an internal standard mixture, as set forth above, in one or more vials or tubes, or in one or more chambers or wells. Alternatively, the container may be configured to hold the reference amount of each internal standard to be assessed separately (e.g., one internal standard per chamber or well).

Some kits include a plurality of containers. For example, some kits include one or more containers having the internal standards. In addition, some kits include one or more containers having the internal standards and an additional container to be used in measurement of the internal standards and quantitation of the one or more metabolites to be assessed in a subject sample (e.g., a multi-welled plate or another tube or vial). In some kits, there is a single container that is used to contain the one or more internal standards and used in measurement of the internal standards and quantitation of the one or more metabolites to be assessed in a subject sample.

In kits where the container is a multi-welled or multi-chambered container, the reference amounts of the metabolites to be assessed may be located in one or more wells or chambers upon distribution of the kit for use. In some kits, the reference amounts of the metabolites to be assessed must be dispersed into one or more wells or chambers in using the kits.

The container of the kit can also be configured to accept a biological sample from at least one subject. For example, where the container of the kit includes multiple chambers or wells, a biological sample from a subject may be distributed into one or more chambers or wells. In some instances, one or more amounts of a subject sample may be distributed into a plurality of chambers or wells. The container of the kit is generally configured to accept fluid samples (e.g., fluid biological samples or solid biological samples that have been processed to obtain a fluid for analysis).

Some kits also include reagents useful for measurement of the internal standards and biomarkers and quantitation of the one or more metabolites to be assessed in a subject sample. These reagents may be included in the kit in one or more additional containers.

An example kit comprises a plurality of internal standards, each provided in a separate container or in the same container. The analytical container will be a microtiter plate configured for use with either a GC-MS or LC-MS device. The microtiter plate will have a sufficient number of wells to receive at least one internal standard. The internal standards will have known concentrations and will be used to dispense a known amount of each internal standard into separate wells of the microtiter plate. After dispensing the internal standards into the analytical container, a portion of the subject sample can also be dispensed into the microtiter plate. Either a single portion of a subject sample is dispensed or a plurality of portions can be dispensed. If a plurality of portions is dispensed into the microtiter plate, each portion may be dispensed into a separate well. In addition, if a plurality of portions is dispensed into the microtiter plate, each portion may be of a different amount.

Example 16 Use of Kits

Kits may be used to perform the methods of the invention to provide a diagnosis or risk prediction for a subject having, or risk of developing, diabetes by enabling quantitation of the metabolites in a metabolite profile. For example, kits of the invention may be used to determine if a subject has high risk of developing diabetes. In addition, kits of the invention may be used to determine if a subject has diabetes. In addition, kits of the invention may be used to determine if a subject having diabetes is responding to a treatment for diabetes.

A biological sample obtained from a subject having, or of high risk of developing, diabetes can be assessed using the kits of the invention. The sample may be a fluid sample (e.g., plasma or serum). In some uses of the kits, the metabolite profile in a subject sample may be assessed without processing of the sample. In other uses of the kits, the metabolite profile in a subject sample may require processing of the sample before being assessed.

A physician may take a sample from a subject and send the sample to a clinical laboratory for testing using the kits of the invention. Alternatively, the physician may be located at a clinical or medical facility that can perform testing using the kits of the invention.

The kits may be used to run a variety of tests to measure the amount of one or more metabolites in a subject sample. For example, the kits may be used to run a spectral analysis of a subject sample. Some kits are configured for spectral analyses such as gas chromatography and/or liquid chromatography. For example, a kit may be configured for LC-TQMS analysis of the metabolites of interest in a subject sample. Alternatively, kits may be configured so that analytical tests specific for different types of metabolites can be conducted (e.g., enzymatic, chemical, colorimetric, fluorometric, etc.) to measure the amount of the metabolites of interest in a subject's sample. In some uses, the internal standards included in the kit are used as positive controls for the analytical test performed to measure the amount of the metabolites of interest in a subject sample. In some uses, the internal standards included in the kit are used to help calibrate and/or measure the amount of the metabolites of interest in a subject sample. Depending on the type of analytical tests to be conducted to measure the metabolites of interest in a subject sample, different components used to conduct the analytical tests can be assembled into the kit with the one or more internal standards and the container.

The data obtained from the analytical tests performed using the kits is the amount of each of one or more metabolites of interest (i.e., metabolite markers) in a subject sample. This data can be compared to reference biomarker levels in healthy subjects.

After the data from the analytical tests performed using the kit are obtained (i.e., metabolite profile for the subject sample (i.e., amount of each metabolite of interest)), the data can be inputted into a software program located on a computer terminal in the laboratory to generate a test result report, which can then be provided to the physician or the individual. Once the physician receives the test result report from the clinical laboratory, the physician can evaluate the subject's physical status. Based on the metabolite profile of the subject's sample assessed, which, as noted above, the test result report may indicate to the physician that the subject either does not have or does have high risk of developing diabetes, that the subject is responding to a particular treatment for diabetes (e.g., surgical treatment, medicine treatment, etc.). The physician can then, based on the individual's status indicated by the test result report, provide suggestions or select an appropriate treatment for the subject, if necessary.

Example 17 Correlating Risk by Comparing a Biomarker Level to a Comparator Level The 62 overweight/obese subjects in Example 1 had normal metabolic markers at baseline and 50 of them developed diabetes (UO) while 12 remained healthy (HO) according to their re-evaluation after ten years.

Figure 6:
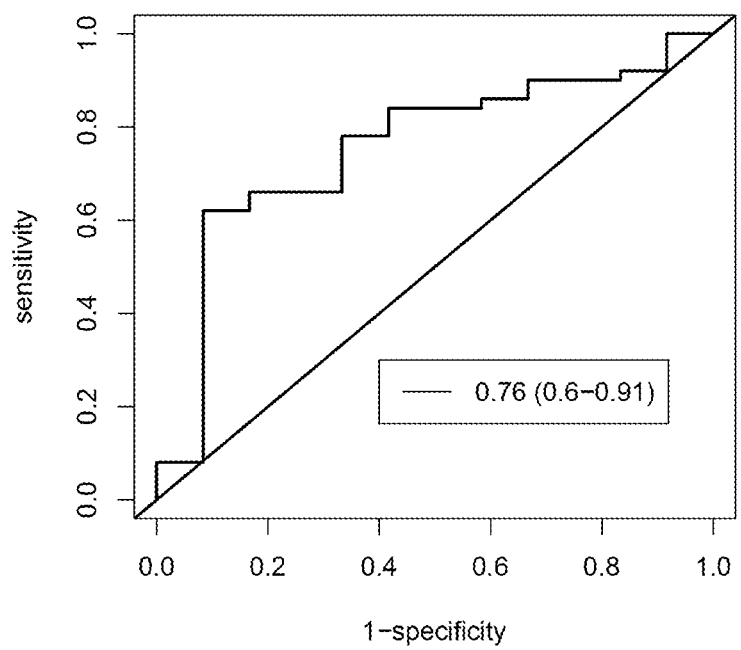
FIG. 6 depicts an ROC curve useful in carrying out a method of the invention. The data was produced from 10 years follow-up serum samples using P/S (C16:0/C18:0) ratio.

P/S ratio (C16:0/C18:0) was selected as a biomarker and Receiver Operating Characteristic (ROC) analysis was further applied to evaluate the performance of the P/S ratio in discriminating those 50 subjects who developed diabetes after 10 years from the 12 remained healthy individuals. The resultant ROC curve area of the P/S ratio was 0.76 (0.60-0.91) (FIG. 6). According to the Youden's index (maximal value of Sensitivity+Specificity−1) from the ROC model, the optimal threshold of the P/S ratio was 1.15, which was used as a comparator value. Thus, overweight/obese subjects who have the P/S ratio greater than 1.15 may have high risk of diabetes in the future.

Example 18 Evaluating Diabetes Risk Using a Model for Scoring of a Multi-Biomarker Panel The 62 overweight/obese subjects in Example 1 had normal metabolic markers at baseline and 50 of them developed diabetes (UO) while 12 remained healthy (HO) according to their re-evaluation after ten years.

A panel comprising P/S ratio (C16:0/C18:0) and TG was selected.

Using logistical regression method, selected markers were combined as a panel and modeled according to the formula $\beta_1 X_1 + \beta_2 X_2 + \ldots + \alpha$, where X denoting the absolute concentration or standardized value for the jth biomarker, $\beta_j$ denoting the coefficient from the regression model, and $\alpha$ denoting a constant value.

The model developed had the formula: Score=1.79*TG+3.67*P/S−4.57

Figure 7:
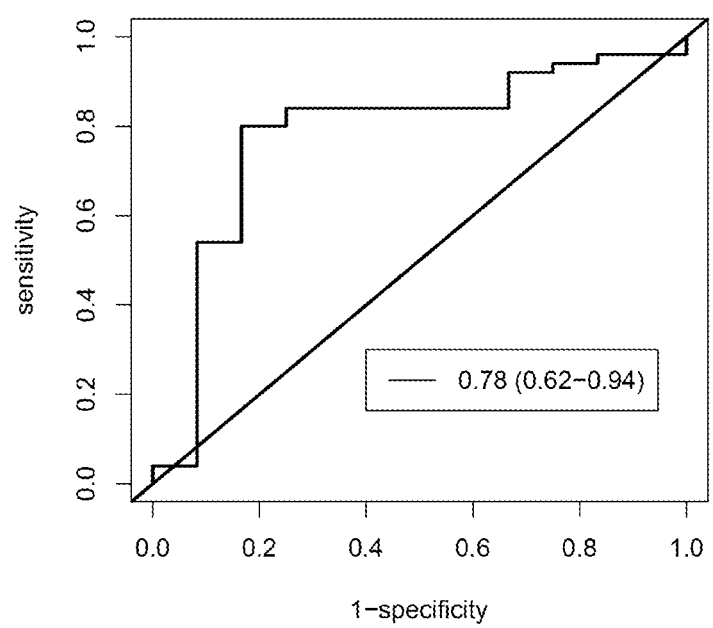
FIG. 7 depicts an ROC curve useful in carrying out a method of the invention. The data was produced from 10 years follow-up serum samples using the combination of P/S (C16:0/C18:0) ratio and TG.

ROC analysis was further applied to evaluate the performance of the calculated score in discriminating those 50 subjects who developed diabetes after 10 years from the 12 remained healthy individuals. The resultant ROC curve area of the combined score was 0.78 (0.62-0.94) (FIG. 7). According to the Youden's index (maximal value of Sensitivity+Specificity−1) from the ROC model, the optimal threshold of the score was 1.58. Thus, overweight/obese subjects who have a score greater than 1.58 are identified has having high risk of developing diabetes.

A sample is obtained from the subject and the P/S level and TG level is measured. The measured levels are input into the model formula to obtain a score as an output. The subject is identified as high risk for developing diabetes if the score is greater than 1.58.

Example 19 Evaluating Diabetes Risk Using a Model for Scoring of a Multi-Biomarker Panel The 62 overweight/obese subjects in Example 1 had normal metabolic markers at baseline and 50 of them developed diabetes (UO) while 12 remained healthy (HO) according to their re-evaluation after ten years.

A panel was selected comprising P/S ratio (C16:0/C18:0), O/S ratio (C18:1 n9/C18:0) and DGLA/AA ratio (C20:3 n6/C20:4 n6).

Using logistical regression method, selected markers were combined as a panel and modeled according to the formula $\beta_1 X_1 + \beta_2 X_2 + \ldots + \alpha$, where X denoting the absolute concentration or standardized value for the jth biomarker, $\beta_j$ denoting the coefficient from the regression model, and a denoting a constant value.

The model developed had the formula: Score=0.50*C16: 0/C18:0+5.28*C18:1 n9/C18:0+11.87*C20:3 n6/C20:4 n6−4.37.

Figure 8:
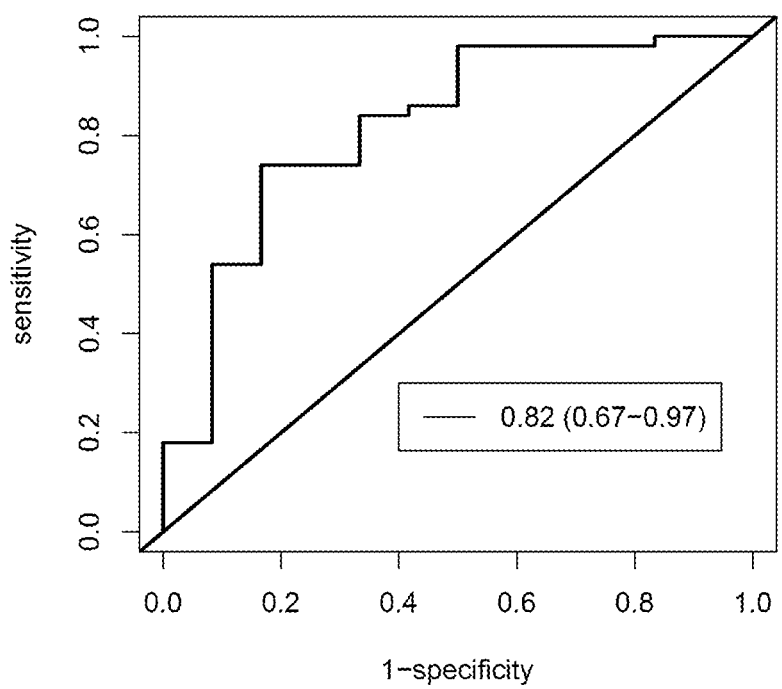
FIG. 8 depicts an ROC curve useful in carrying out a method of the invention. The data was produced from 10 years follow-up serum samples using the combination of P/S (C16:0/C18:0) ratio, O/S ratio (C18:1 n9/C18:0) and DGLA/A ratio (C20:3 n6/C20:4 n6)

ROC analysis was further applied to evaluate the performance of the calculated score in discriminating those 50 subjects who developed diabetes after 10 years from the 12 remained healthy individuals. The resultant ROC curve area of the combined score was 0.82 (0.67-0.97) (FIG. 8). According to the Youden's index (maximal value of Sensitivity+Specificity−1) from the ROC model, the optimal threshold of the score was 1.19. Thus, overweight/obese subjects who have the panel score greater than 1.19 are identified as having high risk of diabetes in the future.

A sample is obtained from the subject and the P/S level O/S level, and DGLA/AA level is measured. The measured levels are input into the model formula to obtain a score as an output. The subject is identified as high risk for developing diabetes if the score is greater than 1.19.

Example 20 GLP1 Production Induced by Treatment with Bile Acids

Several bile acids were tested for their ability to increase production of GLP-1. Without being bound by theory, the inventor believes that compounds which increase the production of GLP-1 provide an anti-diabetic effect.

Figure 13:
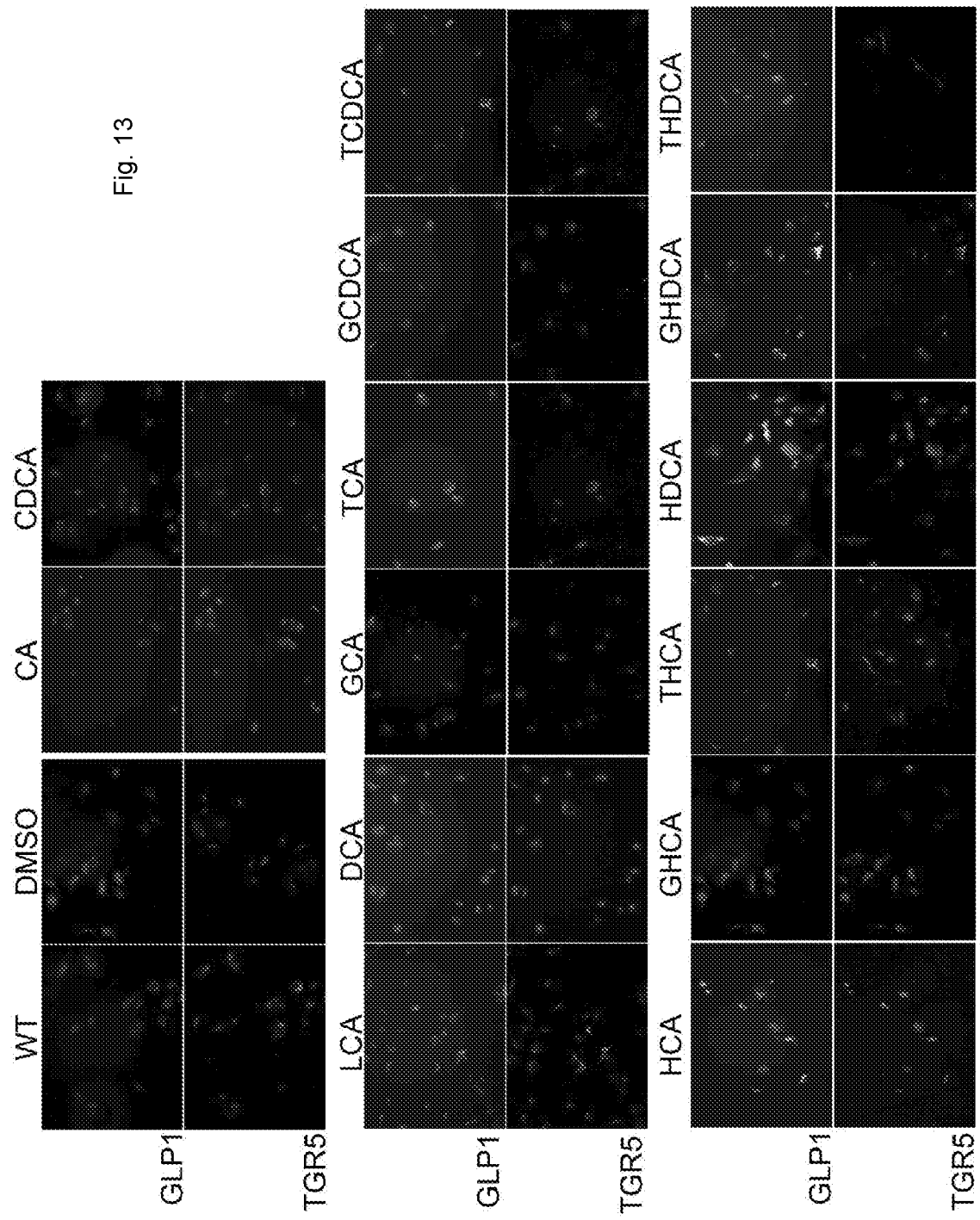
FIG. 13 depicts the levels of TGR5 and GLP1 after treatment with different bile acids and controls (WT, wild-type; and solvent, DMSO).

CCL-241, a human small intestinal normal epithelial cell were treated with 100 μM of different bile acids and compared to that of wild type (WT) and DMSO treatment as controls. The expression of TGR5 and GLP1 were detected by Immunofluorescence staining. The results are shown in FIG. 13. Generally, HCA, HDCA, GHDCA and THDCA exhibited the strongest GLP1-promotion effect. LCA, DCA and TCA also showed substantial GLP-1 promotion effect.

Accordingly, this data demonstrates that subjects having a diabetic condition can be treated with these bile acids or analogs thereof.

Further, subjects that naturally exhibit high levels of these bile acids may be protected or partially protected from developing diabetes. Accordingly, these bile acid may provide useful biomarkers for evaluating diabetes risk.

INCORPORATION BY REFERENCE

The citations (e.g. to patent and non-patent literature) provided herein are hereby incorporated by reference for the cited subject matter.

What is claimed is:

1. A method of determining the risk of a subject developing diabetes comprising:
   a. obtaining a biological sample from the subject;
   b. measuring the level of each biomarker of a panel in the sample, wherein the panel comprises at least one biomarker listed in FIG. 11, wherein said at least one biomarker comprises C16:0/C18:0 ratio;
   c. correlating the measured level with risk of developing diabetes; and
   d. determining the risk of the subject developing diabetes based on the correlation; and
   e. optionally, administering a treatment to the subject determined to be likely to develop diabetes.

2. The method of claim 1, wherein the step of correlating comprises calculating a score from the measured level of the at least one biomarker.

3. The method of claim 2, wherein the score is output from a model wherein the model is executed based on an input of the measured level of each biomarker of the panel.

4. The method of claim 3, wherein the step of determining comprises comparing the calculated score to a threshold score, wherein the subject is determined as likely to develop diabetes if the calculated score exceeds the threshold score.

5. The method of claim 1, wherein the step of correlating comprises comparing the measured level of each of the at least one biomarker to a respective comparator level.

6. The method of claim 1, wherein the panel comprises a panel selected from panels A, D, E, G, H, K, L, N, O, P, W, X, Y, Z, AC, AD, AF, AG, AJ, AK, AM, AN, AO, AV, AW, AX, BE, BF, BK, BN, BO, and BS listed in FIG. 12A-12C.

7. The method of claim 1, wherein the at least one biomarker of FIG. 11 comprises one or more of:
   a. Glycohyodeoxycholic acid ('GHDCA') or % GHDCA of total bile acids;
   b. Glycohyocholic acid ('GHCA') or % GHCA of total bile acids;
   c. Hyodeoxycholic acid ('HDCA') or % HDCA of total bile acids;
   d. Hyocholic acid ('HCA') or % HCA of total bile acids;
   e. Taurohyodeoxycholic acid ('THDCA') or % THDCA of total bile acids;
   f. C18:1 n9/C18:0 ratio;
   g. C20:3 n6/C20:4;
   h. Isoleucine, Leucine, Tyrosine, Valine, and Phenylalanine; and
   i. Total triglycerides ('TG').

8. The method of claim 1, wherein the at least one biomarker of FIG. 11 comprises;
   a. one or more or all of the BCAAs of FIG. 11;
   b. one or both of phenylalanine and tyrosine;
   c. one or more or all of the free fatty acids of FIG. 11;
   d. one or more or all of the bile acids of FIG. 11;
   e. TG; or
   f. a combination of any two or three of a)-e).

9. The method of claim 1, wherein the at least one biomarker of FIG. 11 comprises:
   a. GHDCA or % GHDCA of total bile acids, THDCA or % THDCA, HDCA or % HDCA of total bile acids, HCA or % HCA of total bile acids, GHCA or % GHCA, and THCA or % THCA;

b. Palmitic acid (C16:0), Stearic acid (C18:0), Oleic acid (C18:1 n9), dihomo-γ-linolenic acid (C20:3 n6), and Arachidonic acid (C20:4 n6);
c. Isoleucine, Leucine, Tyrosine, Valine, and Phenylalanine;
d. TG;
e. a combination of a) and b), a) and c), b) and c), or each of a), b), and c);
f. a combination of (a) and (b), (a) and (c), (a) and (d), (b) and (c), (b) and (d), or (c) and (d);
g. a combination (a), (b), and (c);
h. a combination (a), (b), and (d);
i. a combination (a), (c), and (d); or
j. a combination (b), (c), and (d).

10. The method of claim 1, wherein the at least one biomarker of FIG. 11 comprises:
a. one or more of GHDCA or % GHDCA of total bile acids, THDCA or % THDCA, HDCA or % HDCA of total bile acids, HCA or % HCA of total bile acids, GHCA or % GHCA, and THCA or % THCA
b. one or more of Oleic acid (C18:1 n9), dihomo-γ-linolenic acid (C20:3 n6), and Arachidonic acid (C20:4 n6);
c. one or more of Isoleucine, Leucine, Tyrosine, Valine, and Phenylalanine;
d. TG;
e. a combination of a) and b), a) and c), b) and c), or each of a), b), a
f. a combination of (a) and (b), (a) and (c), (a) and (d), (b) and (c), (b) and (d), or (c) and (d);
g. a combination (a), (b), and (c);
h. a combination (a), (b), and (d);
i. a combination (a), (c), and (d); or
j. a combination (b), (c), and (d).

11. The method of claim 1, wherein the subject is any of:
a. metabolically healthy;
b. overweight;
c. obese;
d. not overweight;
e. not obese;
f. a) and b), or a) and c), and
g. a) and d), or a) and e).

12. A method of monitoring diabetes treatment of a subject comprising:
a. obtaining a first biological sample from the subject and a second biological sample from the subject, wherein the first biological sample is obtained from the subject prior to the subject receiving a diabetes treatment and wherein the second biological sample is obtained from the subject following the subject receiving the diabetes treatment;
b. measuring the level of at least one biomarker of FIG. 11 in the first sample and the second sample, wherein said at least one biomarker comprises C16:0/C18:0 ratio;
c. comparing the measured level of the at least one biomarker in the first sample to the measured level of the at least one biomarker in the second sample;
d. determining the efficacy of the treatment based on a deviation in the measured level of the at least one biomarker in the first sample relative to the measured level of the at least one biomarker in the second sample; and
e. changing or discontinuing the treatment if the efficacy is determined to be below a threshold.

13. The method of claim 4, further comprising a step of administering a diabetes treatment to the subject when the calculated score exceeds the threshold score.

14. The method of claim 6, further comprising a step of administering, to the subject determined to be likely to develop diabetes, a treatment selected from the group consisting of metabolic surgery, carbohydrate restriction, dietary calorie restriction, a diet with less than 20 grams carbohydrate per day, an exercise regimen, and an anti-diabetic agent.

15. The method of claim 7, further comprising a step of administering, to the subject determined to be likely to develop diabetes, a treatment selected from the group consisting of metabolic surgery, carbohydrate restriction, dietary calorie restriction, a diet with less than 20 grams carbohydrate per day, an exercise regimen, and an anti-diabetic agent.

16. The method of claim 8, further comprising a step of administering, to the subject determined to be likely to develop diabetes, a treatment selected from the group consisting of metabolic surgery, carbohydrate restriction, dietary calorie restriction, a diet with less than 20 grams carbohydrate per day, an exercise regimen, and an anti-diabetic agent.

17. The method of claim 9, further comprising a step of administering, to the subject determined to be likely to develop diabetes, a treatment selected from the group consisting of metabolic surgery, carbohydrate restriction, dietary calorie restriction, a diet with less than 20 grams carbohydrate per day, an exercise regimen, and an anti-diabetic agent.

18. The method of claim 10, further comprising a step of administering, to the subject determined to be likely to develop diabetes, a treatment selected from the group consisting of metabolic surgery, carbohydrate restriction, dietary calorie restriction, a diet with less than 20 grams carbohydrate per day, an exercise regimen, and an anti-diabetic agent.

19. The method of claim 1, further comprising a step of administering, to the subject determined to be likely to develop diabetes, a treatment selected from the group consisting of metabolic surgery, carbohydrate restriction, dietary calorie restriction, a diet with less than 20 grams carbohydrate per day, an exercise regimen, and an anti-diabetic agent.

* * * * *